US008778155B2

(12) United States Patent
Tsai et al.

(10) Patent No.: US 8,778,155 B2
(45) Date of Patent: Jul. 15, 2014

(54) DISPOSIBLE BIO-ANALYSIS CARTRIDGE AND INSTRUMENT FOR CONDUCTING BIO-ANALYSIS USING SAME

(75) Inventors: Shou-Kuan Tsai, New Taipei (TW); Varouj D. Amirkhanian, La Crescenta, CA (US)

(73) Assignee: Bioptic, Inc., New Taipei (TW)

( * ) Notice: Subject to any disclaimer, the term of this patent is extended or adjusted under 35 U.S.C. 154(b) by 11 days.

(21) Appl. No.: 13/212,210

(22) Filed: Aug. 18, 2011

(65) Prior Publication Data

US 2012/0168312 A1    Jul. 5, 2012

Related U.S. Application Data

(63) Continuation-in-part of application No. 13/016,944, filed on Jan. 28, 2011.

(60) Provisional application No. 61/376,551, filed on Aug. 24, 2010, provisional application No. 61/437,549, filed on Jan. 28, 2011, provisional application No. 61/437,576, filed on Jan. 28, 2011.

(51) Int. Cl.
*B03C 5/02* (2006.01)
*G01N 27/447* (2006.01)

(52) U.S. Cl.
CPC .... *G01N 27/44721* (2013.01); *G01N 27/44756* (2013.01)
USPC ........... 204/451; 204/601; 204/452; 204/453; 204/454; 204/455

(58) Field of Classification Search
USPC .................................. 204/451–455, 601–605
See application file for complete search history.

(56) References Cited

U.S. PATENT DOCUMENTS

| 4,675,300 A * | 6/1987 | Zare et al. ...................... 204/452 |
| 2003/0116436 A1* | 6/2003 | Amirkhanian et al. ....... 204/452 |
| 2004/0115648 A1 | 6/2004 | Mooney et al. |
| 2005/0047973 A1 | 3/2005 | Schulz et al. |
| 2010/0170799 A1 | 7/2010 | Amirkhanian et al. |

FOREIGN PATENT DOCUMENTS

WO    2011/094648    8/2011

OTHER PUBLICATIONS

International Search Report of Counterpart PCT App. No. PCT/US2011/048162.

* cited by examiner

*Primary Examiner* — Bach Dinh
(74) *Attorney, Agent, or Firm* — Liu & Liu

(57) ABSTRACT

A cartridge-based bio-separation system configured to utilize a pen shaped bio-separation cartridge that is easy to assemble and use with no moving parts and that has an integrated reagent (separation buffer) reservoir. The cartridge includes a body, defining an opening as a detection window for receiving external detection optics, at least one capillary column supported in the body, having a first end extending beyond a first end of the body, wherein the detection window exposes a section along the capillary column, to which the external optics are aligned through the detection window, and a reservoir attached to a second end of the body in fluid flow communication with a second end of the capillary column. The reservoir is structured to be coupled to an air pressure pump that pressurizes the gel reservoir to purge and fill the capillaries with buffer as the separation support medium.

21 Claims, 23 Drawing Sheets

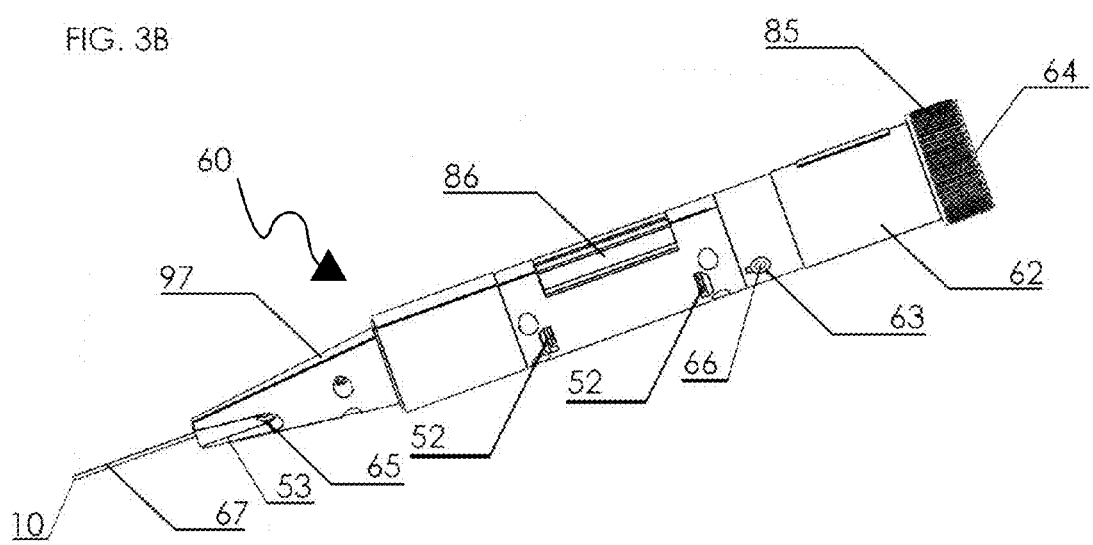

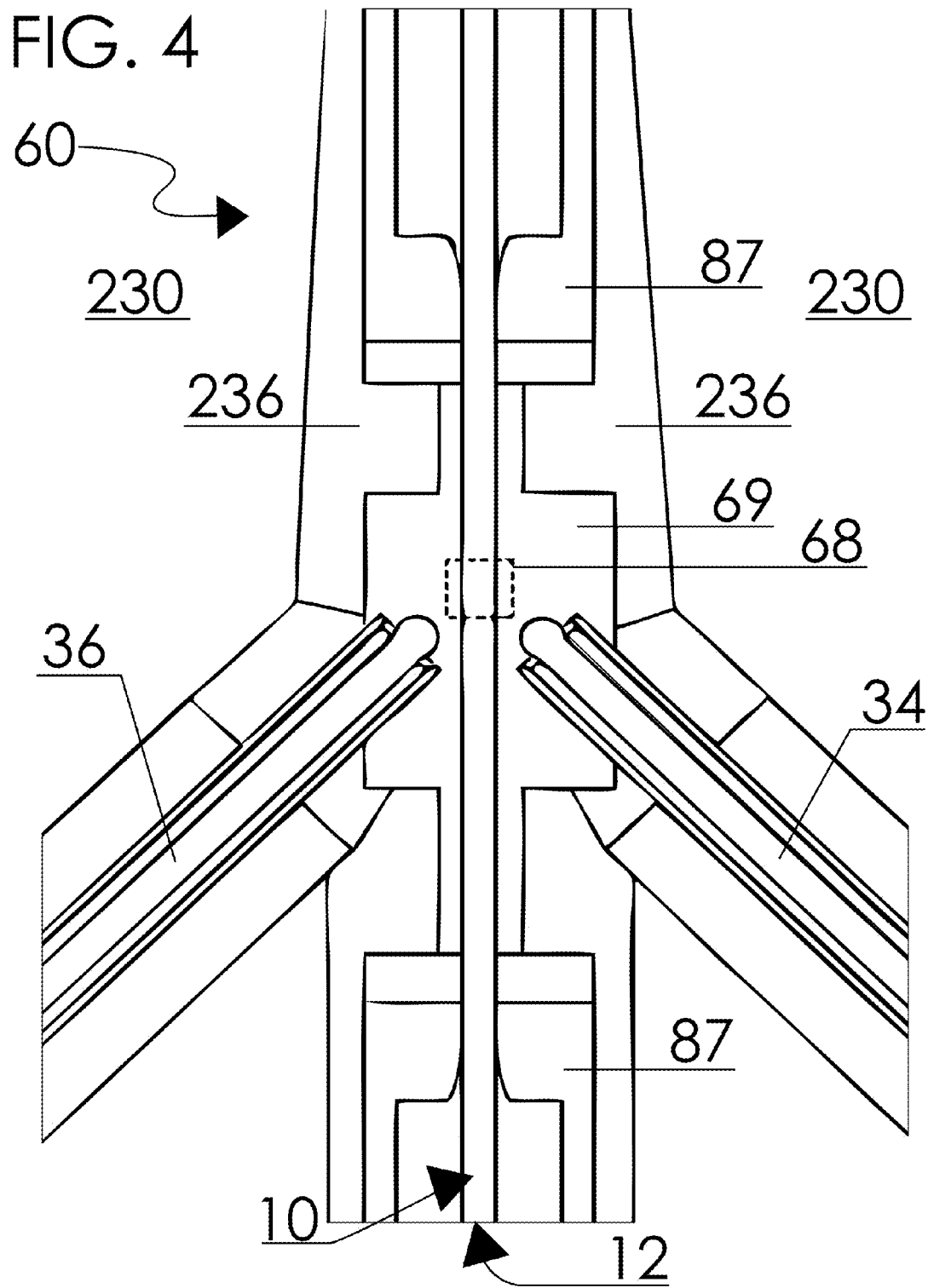

DISPOSABLE BIO-ANALYSIS CARTRIDGE AND INSTRUMENT FOR CONDUCTING BIO-ANALYSIS USING SAME

PRIORITY CLAIM

This application claims the priority of (a) U.S. Provisional Patent Application No. 61/376,551 filed on Aug. 24, 2010; (b) U.S. Provisional Patent Application No. 61/437,549 filed on Jan. 28, 2011; and (c) U.S. Provisional Patent Application No. 61/437,576 filed on Jan. 28, 2011. This application is also a continuation-in-part application claiming the priority of U.S. patent application Ser. No. 13/016,944 filed on Jan. 28, 2011. These and other documents referenced herein are fully incorporated by reference as if fully set forth herein.

BACKGROUND OF THE INVENTION

1. Field of the Invention

The present invention relates to instruments for bio-analysis involving detection and analysis of bio-separation through a separation channel, and more particularly to capillary electrophoresis instruments.

2. Description of Related Art

Currently, most of bio-separation tools applied in the laboratories utilize slab gel based electrophoresis technologies, which have routinely been used for bio-analysis of bio-molecules (i.e. DNA, Protein & Carbohydrate) applications since their inception more than 20 years ago. However, slab gel electrophoresis for bio-analysis is labor intensive and needs to be drastically improved in terms of resolving power, throughput and cost per sample.

Capillary electrophoresis (CE) is a micro fluidic approach to gel-electrophoresis (micro-channel device to simplify gel-electrophoresis), whose greatest advantage is its diverse range of applications. CE technology is commonly accepted by the biotechnology industry specifically in the nucleic acid-based testing as a reliable, high resolution and highly sensitive detection tool, and CE has been applied for protein, carbohydrate and DNA-related analyses such as oligonucleotides analysis, DNA sequencing, and dsDNA fragments analysis. CE is commonly avoided in routine analysis because it is reputed to be a troublesome technique with high failure rates. However this is no longer true because instrument manufacturers have drastically improved instrument design and overall CE knowledge has increased. There are three key factors for reducing failure rate and producing accurate, precise and robust CE data: operator training, system stability, and operation ease of the instrument with low maintenance.

Capillary Electrophoresis Immunoassay Analysis (CEIA) has recently emerged as a new analytical technique, when combined with sensitive detection methods such as Laser Induced Fluorescence (LIF), offers several advantages over the conventional immunoassays. CEIA can perform rapid separations with high mass sensitivity, simultaneously determine multiple analytes and is compatible with automation. Use of CE and florescence labeled peptides can be used to detect abnormal prion protein in the blood of animals. One such CE-based noncompetitive immunoassay for Prion Protein using Fluorescein isithiocyanate (FITC)-labeled Protein A as Fluorescent probe method has successfully been applied for testing blood samples from scrapie-infected sheep.

Further, immunoassays are commonly used in biotechnology for the detection and quantification of host cell contaminants. The free-solution approach by CE with fluorescence type detection has brought an exciting alternative to solid-phase immunoassay. The CE with fluorescent type detection eliminates antigen immobilization and avoids many solid-phase-associated problems. This methodology makes use of either a purified antigen labeled with stable fluorescent dye (i.e. FITC) or an affinity probe labeled with the dye (direct assay).

Without a doubt, CE with laser-induced fluorescence (LIF) is one of the most powerful analytical tools for rapid, high sensitivity and high-resolution dsDNA analysis and immunoassay analysis applications. However, the current selling price for CE-based LIF systems is much more expensive than traditional slab-gel based bio-analysis systems due to the complicated optical detection mechanism. The expensive CE-based systems are thus out of reach for all but a few well-funded laboratories and seems to be a high-cost barrier for the expansion of immunoassay or DNA fragment type analysis applications/business.

U.S. patent application Ser. No. 13/016,944, now published as U.S. Patent Publication No. 20110253540, discloses a simplified, low cost, efficient, highly sensitive, non-moving and stable micro-optical detection configuration for bio-separation (e.g., capillary electrophoresis) through a separation channel (e.g., defined by a column) filled with a separation support medium (e.g., a liquid or sieving gel including a running buffer). More particularly, the disclosed invention is directed to an improved detection configuration that includes optics for application of incident radiation at and detection of output radiation from a detection zone along the separation channel, for the detection of radiation emitted by sample analytes (e.g., radiation induced fluorescence emission). In one aspect of the disclosed invention, the direction of incident radiation (e.g., from a laser or LED source), the axis of the separation channel at the detection zone, and the direction of collection of the output radiation are all substantially in the same plane. In one embodiment, the incident radiation is provided to the detection zone and/or the output radiation is collected from the detection zone, using light guides in the form of optical fibers. In an embodiment, the detection configuration of the present invention has optical fibers positioned at opposite sides of the detection zone along the separation channel. The optical fibers may be positioned at less than 180 degrees (e.g., 40 to 160 degrees, such as 120 degrees) apart from each other for high detection sensitivity. In another aspect of the disclosed invention, the detection configuration of the present invention incorporates ball-end optical fibers to provide incident radiation and collection of output radiation. In a further aspect of the disclosed invention, the detection optics configuration of the present invention may be implemented in an improved bio-separation instrument, in particular a capillary electrophoresis instrument.

Based on the above disclosed detection technology, there is a need for a capillary electrophoresis system that is simple and less expensive to operate (i.e. low cost per sample run), providing rapid analysis with high efficiency, sensitivity and throughput.

SUMMARY OF THE INVENTION

The present invention provides a simplified, low cost, high efficiency, highly sensitive, high throughput bio-separation system (e.g., capillary electrophoresis system). The bio-separation system includes an instrument that is provided with a detection configuration that includes optics for application of incident radiation at and detection of output radiation from a detection zone along the separation channel, for the detection of radiation emitted by sample analytes (e.g., radiation induced fluorescence emission), without requiring fine alignment of the optics to the separation column. The instrument is configured to conduct bio-separation in the separation channel of the bio-separation cartridge in an automated manner.

In one aspect of the present invention, the present invention is directed to cartridge-based bio-separation system configured to utilize a reliable, compact, simplified, removable, portable, interchangeable, reusable, low cost, recyclable and/or disposable bio-separation cartridge that is easy to assemble and use with no moving parts and that has an integrated reagent (separation buffer) reservoir. The bio-separation cartridge includes at least one separation channel defined therein. In one embodiment, the bio-separation cartridge is generally the shape of a pen. In one embodiment, the overall size of the cartridge is characterized by the separation channel being no longer than 30 cm, preferably in the range of 15 to 20 cm. The bio-separation system includes an instrument that is provided with a detection configuration that includes optics for application of incident radiation at and detection of output radiation from a detection zone along the separation channel, for the detection of radiation emitted by sample analytes (e.g., radiation induced fluorescence emission) without requiring fine alignment of optics to the capillary column. The instrument is configured to conduct bio-separation in the separation channel of the bio-separation cartridge in an automated manner.

In another aspect of the present invention, the chemistry of the medium and the characteristics of the capillaries (e.g., capillary size, coating and length) are defined for each cartridge. Different cartridges can be easily interchanged for use in the bio-separation system to suit the particular sample based separation. The reservoir is structured to be coupled to an air pressure pump that pressurizes the gel reservoir to purge and fill the capillaries with buffer as the separation support medium. The cartridge does not require detection optics to be integrated into the cartridge, and the separation channel does not require fine alignment with respect to the detection zones. In one embodiment, the cartridge does not include integrated detection optics.

In one embodiment, the bio-separation cartridge is provided with a single separation channel. In one embodiment, a capillary column that is supported by and within the cartridge defines the separation channel. In one embodiment of the present invention, the bio-separation system is for capillary electrophoresis separation and analysis, and the instrument therein is structured to utilize the capillary cartridge to conduct capillary electrophoresis separation, detection and analysis in an automated manner. In another embodiment, the structure of the single channel cartridge could be extended to structure a multi-channel (e.g., 4, 8 or 12) cartridge (e.g., having multi-capillary columns) for higher throughout applications.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

FIGS. 3A and 3B are perspective views of the capillary cartridge in accordance with one embodiment of the present invention.

FIG. 4 is an axial plane sectional view at the detection region in the capillary cartridge of FIG. 3.

DETAILED DESCRIPTION OF THE PREFERRED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides a simplified, low cost, high efficiency, highly sensitive, high throughput bio-separation system (e.g., capillary electrophoresis system). The bio-separation system includes an instrument that is provided with a detection configuration that includes optics for application of incident radiation at and detection of output radiation from a detection zone along the separation channel, for the detection of radiation emitted by sample analytes (e.g., radiation induced fluorescence emission), without requiring fine alignment of the optics to the separation column. The instrument is configured to conduct bio-separation in the separation channel of the bio-separation cartridge in an automated manner.

For purpose of illustrating the principles of the present invention and not limitation, the present invention is described by reference to embodiments directed to capillary electrophoresis using a capillary separation column. Further, the present invention will be described, without limitation, in connection with radiation induced fluorescence detection (e.g., using a laser or LED source). Fluorescence is a spectrophotometric method of analysis where the molecules of the analytes are excited by irradiation at a certain wavelength and emit radiation at a different wavelength. The emission spectrum provides information for both qualitative and quantitative analysis. Generally, the advantage of fluorescence detection over absorbance detection is the superior detectability (detection sensitivity). For efficient fluorophores, single molecule detection in small volumes has been demonstrated. This is in part because fluorescence signal is measured against a relatively dark background, as a result of the emitted radiation being detected at a wavelength that is different from the wavelength of the incident radiation (e.g., the wavelength of the emitted fluorescence is at longer wavelengths than the excitation radiation).

System Overview

Figure 1:
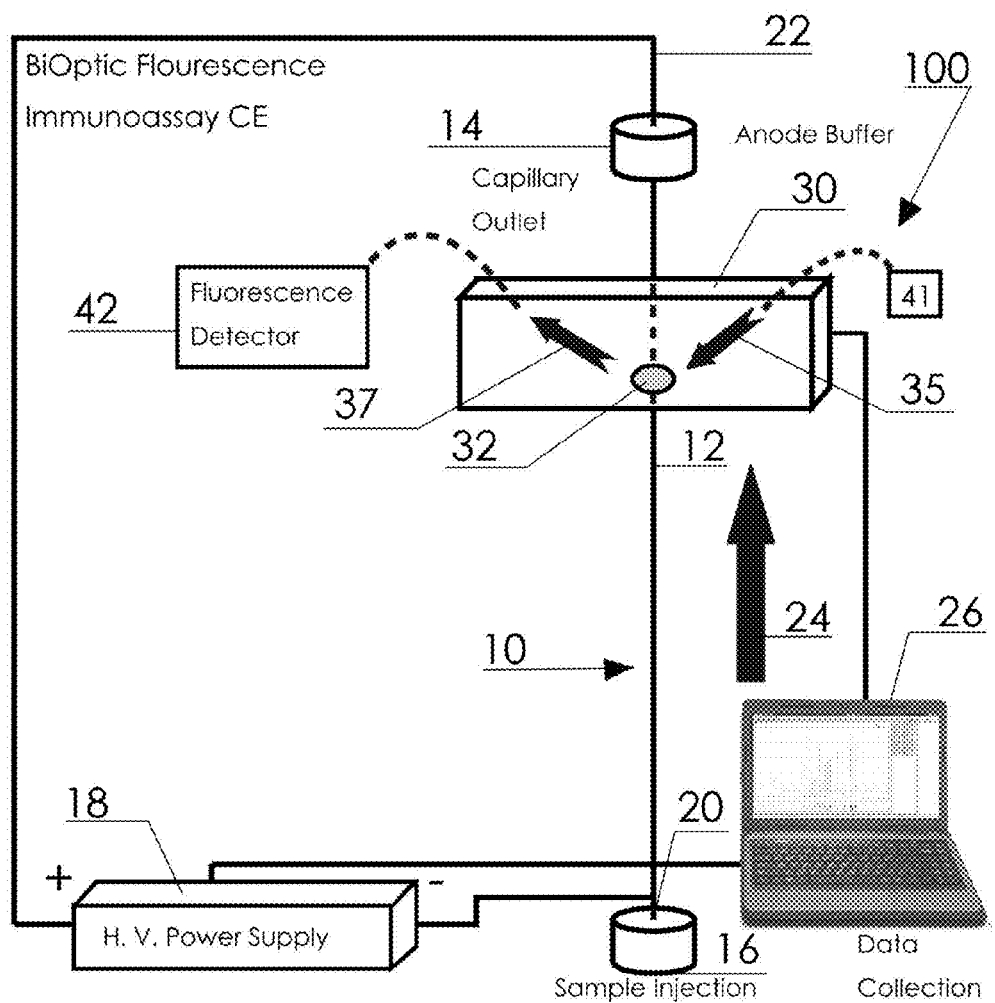
FIG. 1 is a schematic view of a capillary electrophoresis system that incorporates the instrument and cartridge in accordance with one embodiment of the present invention.

Referring to FIG. 1, a capillary electrophoresis (CE) system 100 that incorporates the novel detection configuration of the present invention is schematically illustrated. In the illustrated embodiment, the CE system 100 generally comprises a capillary separation column 10 (e.g., 200-500 μm O.D.), which defines an internal separation channel 12 (e.g., 10-150 μm I.D.). The capillary column 10 may be made of fused silica, glass, polyimide, or other ceramic/glassy materials. The inside walls of the separation column 10 (i.e., the walls defining the separation channel 12) may be coated with a material that can build up an electrostatic charge to facilitate electrophoresis and/or electrokinetic migration of the sample components. The separation channel 12 may be filled with a separation support medium, which may be simply a running buffer, or a sieving gel matrix (of a linear or non-linear polymeric composition) known in the art. The gel buffer is of the "replaceable" type, which can be pushed through the separation column (e.g., defined by the capillary column 10) without appreciably affecting its property as a separation buffer.

One end of the capillary column 10 is coupled to a reservoir 14 of running buffer. The other end of the capillary column 10 is coupled to another reservoir 16, which may alternately contain a sample (to be injected into the separation channel 12) and running buffer (after sample injection, to undertake separation). A power supply 18 supplies a high voltage to the reservoirs 14 and 16 via electrodes 20 and 22.

The mechanism of electrophoresis and radiation induced fluorescence when considered alone are outside the scope of the present invention. For the sake of completeness, it is sufficient to briefly mention the operation of the CE system 100. In operation, a prepared biological sample, tagged with a known fluorophore, is introduced into the far end of the capillary column away from the detection zone, by any of a number of ways that is not part of the present invention (e.g., electrokinetic injection from a sample reservoir or physical pressure injection using a syringe pump). When a DC potential (e.g., 1-30 KV) is applied by the power supply 18 to the electrodes 20 and 22, the sample migrates under the applied electric potential along the separation channel 12 in the direction 24 (e.g., sample that is negatively charged travels toward the positive electrode 22 as shown in FIG. 1) and separates into bands of sample components. The extent of separation and distance moved along the separation channel 12 depends on a number of factors, such as migration mobility of the sample components, the mass and size or length of the sample components, and the separation support medium. The driving forces in the separation channel 12 for the separation of samples could be electrophoretic, pressure, or electro-osmotic flow (EOF) means.

When the sample reaches the detection zone 32, excitation radiation is directed via the excitation fiber 34 in a direction 35 at the detection zone 32. The sample components would fluoresce with intensities proportional to the concentrations of the respective sample components (proportional to the amount of fluorescent tag material). The detector 42 detects the intensities of the emitted fluorescence via the emission fiber 36 in a direction 37, at a wavelength different from that of the incident radiation. The detected emitted radiation may be analyzed by known methods. For an automated system, a controller 26 (e.g., in the form of a notebook computer or a desktop computer) having a processor, controls the operations of the various components in the CE system 100 to effect capillary electrophoresis separation and data collection. Such control is well within the knowledge of one skilled in the art given the disclosure of the function and features disclosed herein.

Detection Configuration

Figure 2:
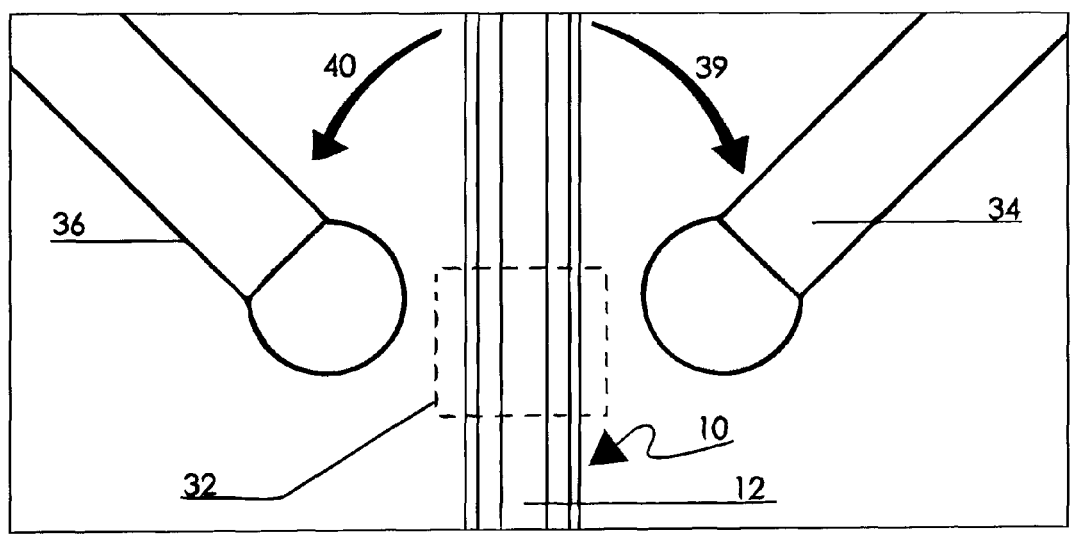
FIG. 2 illustrates the detection region, schematically showing the configuration of the excitation fiber, emission fiber and the capillary column.

In the particular illustrated embodiment in FIG. 1, the detection optics configuration (schematically indicated in the area 30 located about a detection window/zone 32) corresponds to the embodiment illustrated in FIG. 2. Essentially, an optical fiber delivers radiation to the capillary column, and another optical fiber collects radiation from the detection zone. Specifically, the direction 35 of incident radiation (e.g., from a laser or LED source), the axis of the separation channel at the detection zone, and the direction 37 of collection of the output radiation are all substantially in the same plane. In the illustrated embodiment, the detection configuration of the present invention has optical fibers positioned at opposite sides of the detection zone separation channel. In one embodiment, the incident radiation is provided to the detection zone and/or the output radiation is collected from the detection zone, using light guides in the form of optical fibers, in particular ball-ended optical fibers (i.e., optical fibers terminating in a micro ball that is integral to the fiber end in a unitary structure).

Referring also to FIG. 2, a ball-ended fiber (the excitation fiber 34) extends from a radiation source (e.g., LED or laser source 41, schematically shown in FIG. 1) to direct excitation radiation in a direction 35 at the detection zone 32. The ball end of the excitation fiber 34 is positioned at or proximate to the exterior surface of the separation column 10 about the detection zone 32. In the illustrated embodiment, the ball end of the excitation fiber 34 is positioned at a distance spaced from the exterior surface of the separation column 10 (i.e., non-contact mode). In this illustrated embodiment, another ball-ended fiber (the emission fiber 36) extends to a detector (e.g., a fluorescence detector 42, schematically shown in FIG. 1) to collect emitted radiation at a direction 37 from the detection zone 32. The ball end of the emission fiber 36 is positioned at or approximate to the exterior surface of the separation column 10 about the detection zone 32. In the illustrated embodiment, the ball end of the emission fiber 36 is positioned at a distance spaced (in a non-contact mode) from the exterior surface of the separation column 10. Both excitation and emission fibers 34 and 36 with ball tips are positioned at opposite sides of the separation column 10 in a non-contact mode (spaced from the exterior of the capillary column) to reduce background fluorescence and not cause any physical damage to either capillary column or the microball.

In the illustrated embodiment in FIG. 2, the components at the detection zone 32 as shown in FIG. 2 lie in substantially the same plane. Specifically, the longitudinal axis of the excitation fiber 34, the longitudinal axis of the emission fiber 36 and the longitudinal axis of the capillary channel 12, are substantially aligned in the same plane (i.e., substantially coplanar), at least at the region of the detection zone 32. That is, while the lengths of the excitation fiber 34, the emission fiber 36 and the capillary column 10 may be bent overall, however at least near the detection zone region, the axis of the excitation fiber 34, the axis of the emission fiber 36 and the axis of the capillary channel 12 are substantially aligned in the same plane, such that the direction 35 of incident radiation from the excitation fiber 34 towards the detection zone 32, the axis of the separation channel 12 at the detection zone 32, and the direction 37 of collection of the output radiation away from the detection zone along the emission fiber 36 are all substantially in the same plane.

Further, at the detection zone 32, the angle between the axis of the excitation fiber 34 and the axis of the emission fiber 36 are not aligned in a straight line. At least one of the axis of the excitation fiber 34 and the axis of the emission fiber 36 is not perpendicular to the axis of the separation channel 12 at the detection zone 32. In the illustrated embodiment shown in FIG. 2, both the axis of the excitation fiber 34 and the axis of the emission fiber 36 are not perpendicular to the axis of the separation channel, and are at angles 39 and 40, respectively, to the axis of the separation channel 12 at the detection zone 32. The angle 39 and the angle 40 may be substantially the same or different, and may be less than or greater than 90 degrees measured with respect to a reference direction of the axis of the separation channel 12 or a reference section of the capillary column 10 (e.g., the section of capillary column 10 between the fibers 34 and 36 as shown in FIG. 2). For example, the angle 39 may be less than 90 degrees and the angle 40 may be greater than 90 degrees, measured from the same reference section. In the illustrated embodiment in FIG. 2, the angles 39 and 40 are same and substantially in the same plane.

In the embodiment illustrated in FIG. 2, both the excitation fiber 34 and the emission fiber 36 each has a 200 micron diameter core as light guide within an external cladding, and a 350 micron diameter ball shaped tip (i.e., the ratio of the fiber core diameter to the ball diameter is 1:1.75), which comprises fused the core and cladding material. The ball shaped tip has a substantially spherical profile. The ball-end fibers may be formed by using a fusion splicer, or are available from a number of available suppliers. The capillary column 10 has an outside diameter of 200 to 370 micron (e.g., 360 micron) and an internal diameter of 20 to 150 micron (e.g., 75 micron). The tip of the ball end of the excitation fiber 34 is spaced at approximately 50-500 micron from the external surface of the capillary column, and the tip of the ball end of the emission fiber 36 is spaced at approximately 10 to 500 microns (e.g., 50-200 micron) from the external surface of the capillary column. Alternatively, the emission fiber 36 may have a 300 micron diameter core with a 500 micron diameter ball shaped tip at its distal end (i.e., the ratio of the fiber core diameter to the ball diameter is 1:2.5). The angles 39 and 40 each may range from greater than 0 to less than 90 degrees, preferably between 20 to 70 degrees, and more preferably at 30 to 45 degrees. In the illustrated embodiment of FIG. 2, both angles 39 and 40 are about 70 degrees.

In one embodiment, the optical detection system is structured with a super-bright royal blue LED (e.g., Cree XLamp) as excitation radiation source for the fluorescent labeled (FITC) antibody fragment detection. The modular design and fiber optic coupling provides flexibility for exchanging the excitation radiation to a laser module (for LIF applications) or other type of inexpensive light sources.

It has been found that compared with flat-end fibers (bare fiber, with no micro ball lens, the ball-ended fibers (FIG. 2) provide good focusing of incident radiation (light concentration/power density) for the excitation fiber 34 and high collection efficiency (high Numerical Aperture NA) for the emission fiber 36 as a high angle fluorescence collector for increased fluorescence signal collection capability and improved detection sensitivity. Using large core (100-1000 micron) and high NA multi-mode fibers, it allows high power light coupling from LED or laser into the excitation fiber 34. By producing an integrated micro ball lens at the distal output end of the excitation fiber 34, it allows good coupling efficiency inside the separation channel 12 (20-200 micron micro-fluidic channel) for high fluorescence detection sensitivity.

A smaller diameter excitation fiber 34 having 200 micron core diameter with a 330-350 micron diameter ball (see FIG. 2) directed at the capillary separation channel 12 results in a smaller focal spot with higher power density, thereby optimizing the fluorescence excitation signal. If an emission fiber 36 having a 300 micron core diameter and a 500 micron diameter ball lens is used for emission collection, the emission collection efficiency is increased. Comparing to detection configurations disclosed in earlier patents (e.g., U.S. Pat. Nos. 6,184,990; 6,828,567 and 6,870,165), in which the excitation fiber and the emission detection optical axis at 90 degrees out of plane, the present novel approach positions the excitation fiber, emission fiber and the separation channel in substantially the same plane. This configuration provides simplicity in mechanical alignment of the micro-optics with respect to the fluidic channel (glass capillary).

While the illustrated embodiment is directed to detection of the radiation induced fluorescence type, the present invention also applies to other types of detection schemes, such as absorbance detection, in which an optical fiber delivers radiation to the capillary column, and another optical fiber collects radiation from the detection zone.

CE Cartridge

In one aspect of the present invention, the system 100 is a cartridge-based bio-separation system that comprises a CE instrument (e.g., shown in FIGS. 7 to 9) that is configured to utilize a reliable, compact, simplified, removable, portable, interchangeable, reusable, low cost, recyclable and/or disposable bio-separation cartridge that is easy to assemble and use with no moving parts and that has an integrated reagent (separation buffer) reservoir. The bio-separation cartridge could be structured to have an overall size generally conforming to the shape of a pen. The bio-separation cartridge includes at least one separation channel defined therein. The bio-separation system 100 is provided with the above-described detection configuration that includes optics for application of incident radiation at and detection of output radiation from a detection zone along the separation channel, for the detection of radiation emitted by sample analytes (e.g., radiation induced fluorescence emission) without requiring fine alignment of optics to the capillary column. The system 100 is configured to conduct bio-separation in the separation channel of the bio-separation cartridge in an automated manner.

FIGS. 3A to 3H illustrate a single-channel cartridge 60 in accordance with one embodiment of the present invention. A capillary column 10 is supported by and within the cartridge 60. In the illustrated embodiment, the cartridge 60 has a slender and generally longitudinal and cylindrical body 80. While the illustrated body 80 of the cartridge 60 is generally circular cylindrical, it may have other sectional cylindrical profile, such as square, rectangular, hexagonal, elliptical, or other regular and irregular profiles. As illustrated, the body 80 has a body section that has a generally uniform or constant width, with the bottom end of the body being narrower than the uniform width of the body section. The bottom end of the body 80 may be tapered to a narrower section, e.g., terminating in a generally conical portion 97. The capillary column 10 is held by or within the cartridge body 80 generally in line with the longitudinal central axis of the cartridge body 80. The In one embodiment, the overall size of the cartridge is characterized by the separation channel being no longer than 30 cm, preferably in the range of 15 to 20 cm.

Figure 6A:
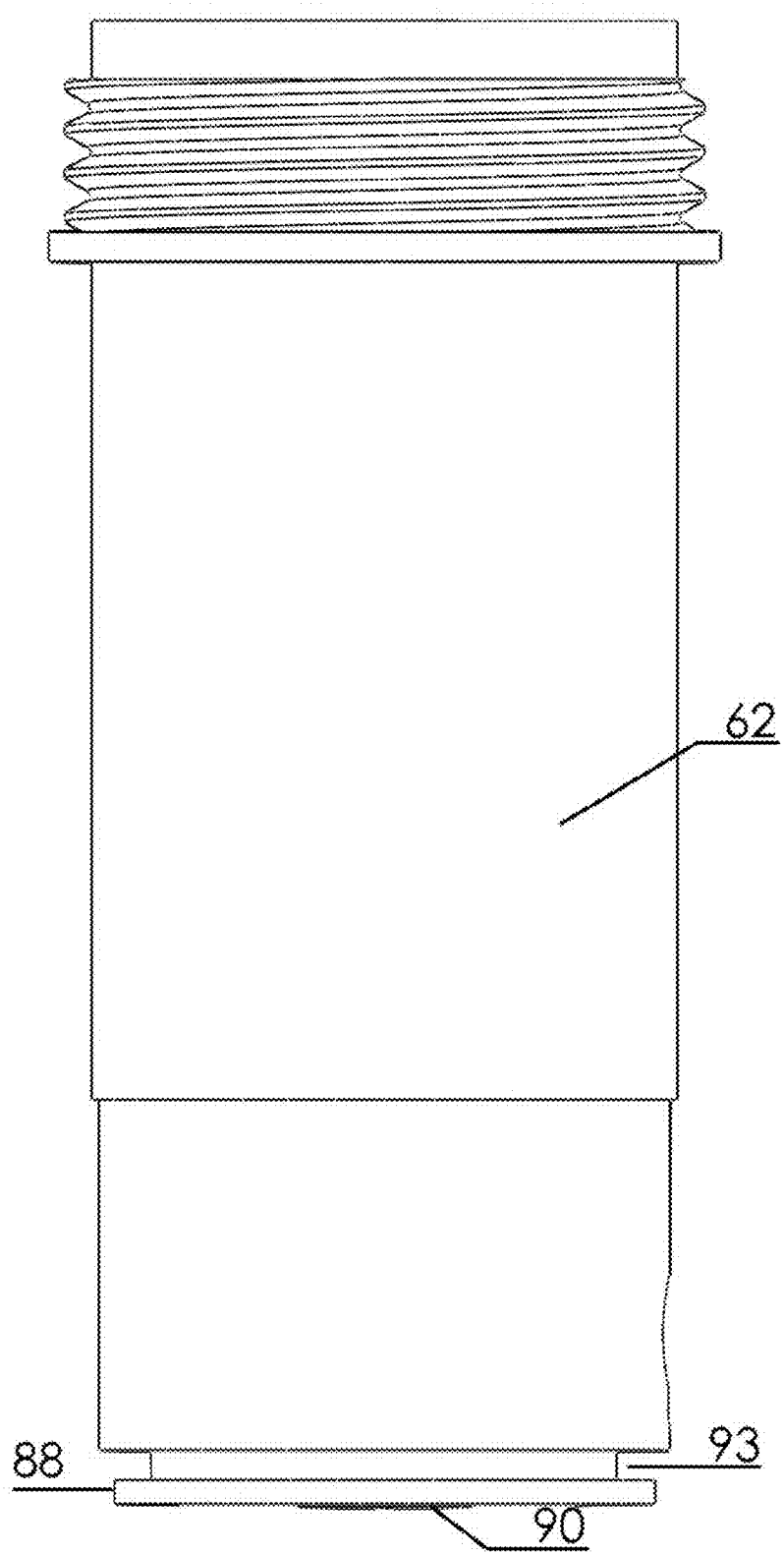
FIGS. 6A and 6B illustrate the structure of the reservoir of the cartridge of FIG. 3, in accordance with one embodiment of the present invention.
Figure 6B:
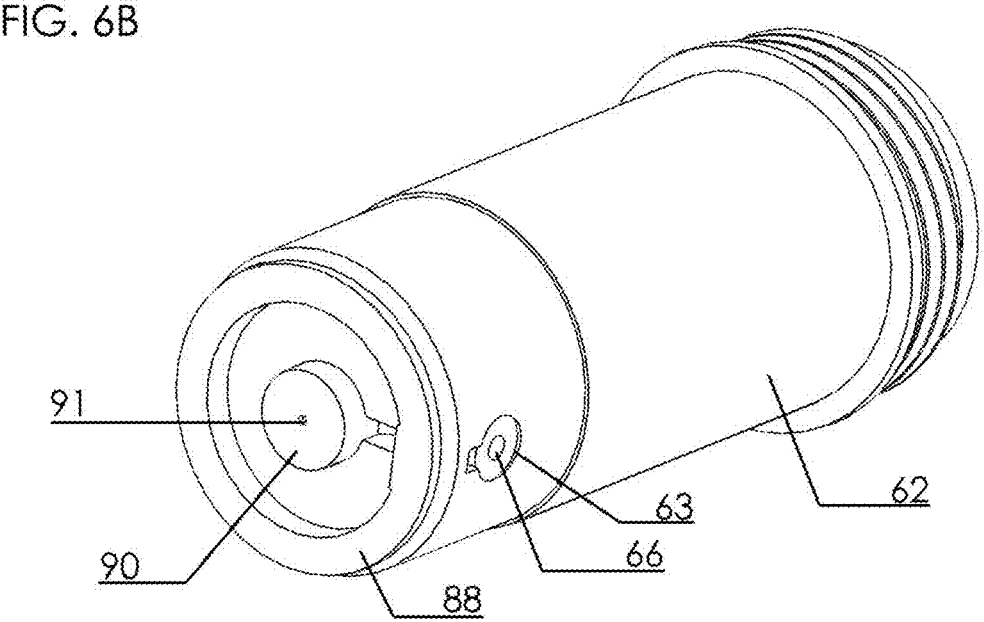

Referring also to FIGS. 6A and 6B, an outlet buffer reservoir 62 is attached to the top end of the body 80. The buffer reservoir 62 includes a cap 85 (e.g., screw-on or plug) that seals the top opening of the reservoir 62, to retain separation support medium (e.g., gel buffer) therein (FIG. 6A shows the reservoir 62 with the cap 85 removed.) The bottom of the reservoir 62 has a rim 89 defining a groove 93, and a center stub 90 having a through hole 91 for receiving the capillary column 10. The reservoir 62 has a port 64 (e.g., a small drilled hole) that is for coupling to an external pressurized gas (e.g., nitrogen) supply (e.g., a gas tank or pump that is part of the CE instrument to be discussed below). (When the cartridge 60 is not used for a while, the port 64 can be sealed by applying a short strip of tape.) The pressurized gas provides the required air pressure to purge and fill the capillary separation channel 12 in the capillary column 10 with the separation support medium (buffer) contained in the reservoir 62. Depending on the viscosity of the separation buffer, pressures of up to 60 PSI can be applied to fill the capillary column 10 through the top buffer reservoir 62. The reservoir 62 is provided with an electrode 66 (anode), which provides electrical contact to the buffer. The electrode 66 has contact surface exposed to external through opening 63.

Figure 5A:
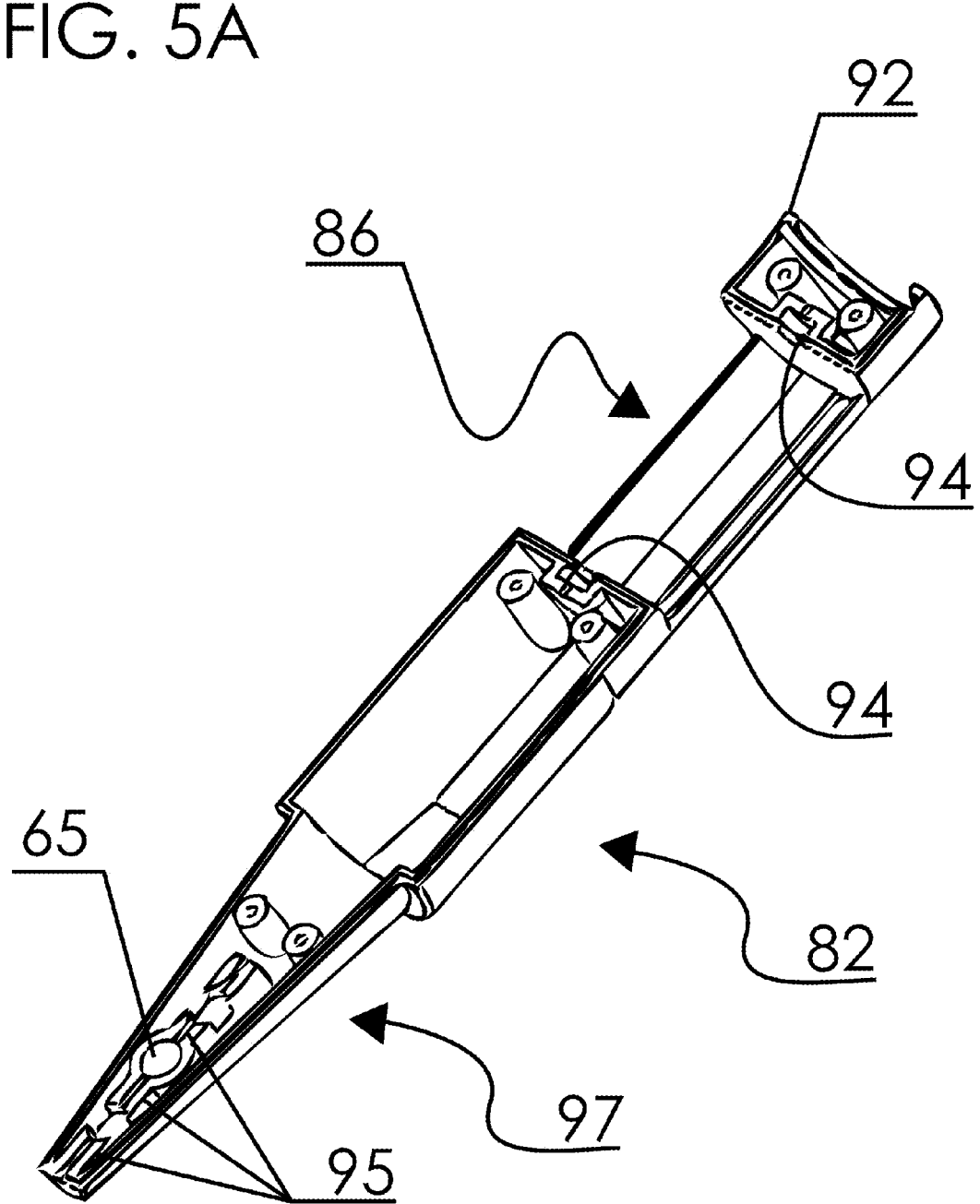
FIGS. 5A and 5B illustrate the inside structure of half shells of the cartridge of FIG. 3, in accordance with one embodiment of the present invention.
Figure 5B:
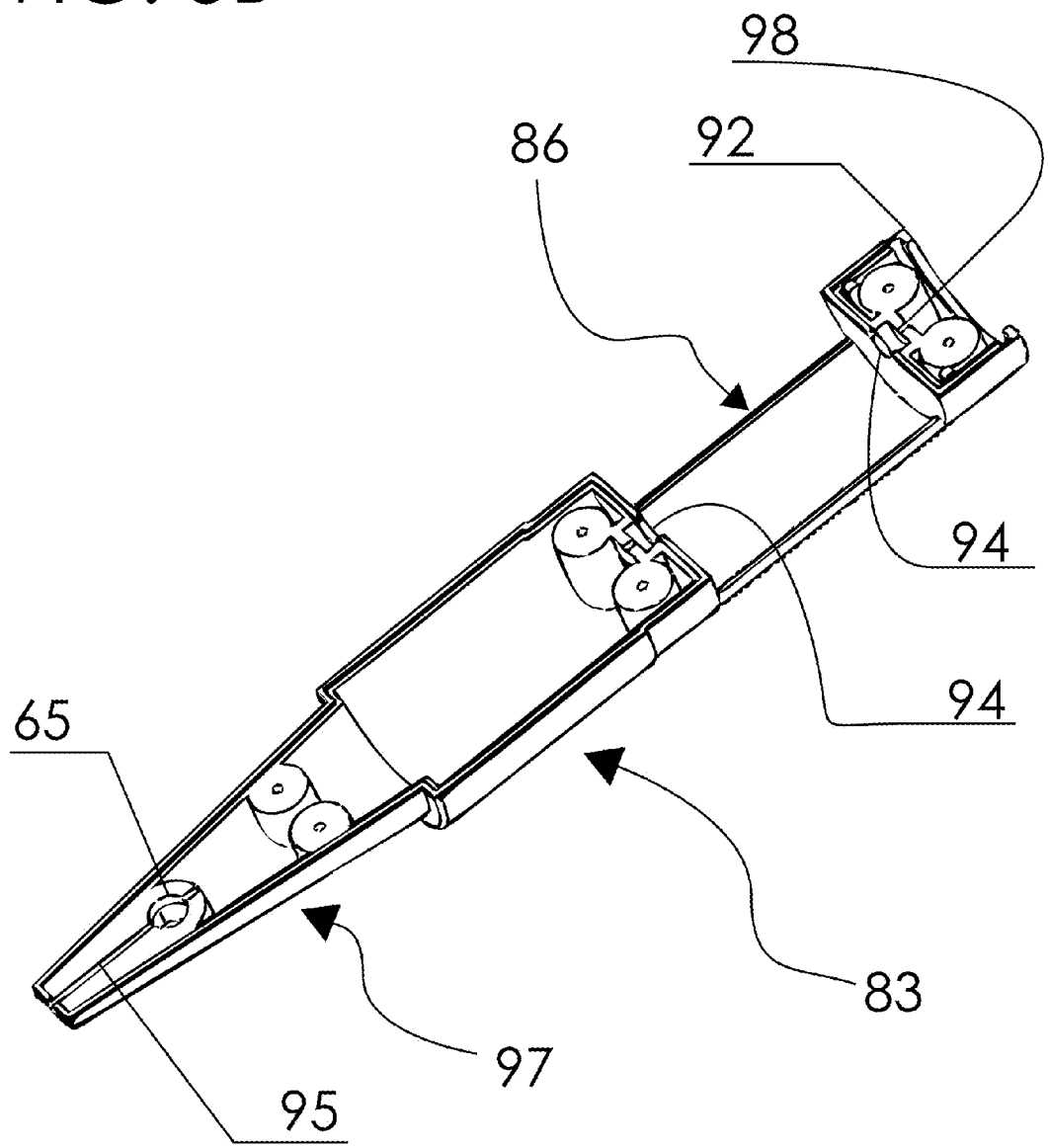

Referring also to FIGS. 5A and 5B that illustrate the internal structures, the body 80 includes two half shells 82 and 83 that are each generally a half cylinder extending to a half conical portion 97. The half shells 82 and 83 define a through opening or window 86 for access to the detection zone 68 by external optics (as will be explained further in connection with the CE instrument discussed below.) The inside of the half shells 82 and 83 are generally hollow. The top ends of the half shells 82 and 83 are each provided with a flange 92, which mates with the groove 93 on the reservoir 62 when the parts are assembled, to securely attached the reservoir 62 to the body 80 of the cartridge 60. Grooves and recesses are provided at appropriate locations along the inside of the half shells 82 and 83 to thread the capillary column 10. At the outside surface of the half shell 82 is an alignment slot 50 and indexing recesses 51 to provide guides to facilitate positive and accurate positioning and alignment of the detection window 86 in the cartridge 60 with respect to the CE instrument when the cartridge 60 is inserted into the CE instrument. Similarly, at the outside of the half shell 83, indexing recesses 52 are provided for alignment and positioning the detection window 86 within the CE instrument. Further, an alignment/indexing recess 53 are provided to facilitate alignment and positioning of the electrode 67 to the external power source provided in the CE instrument.

Figure 3A:
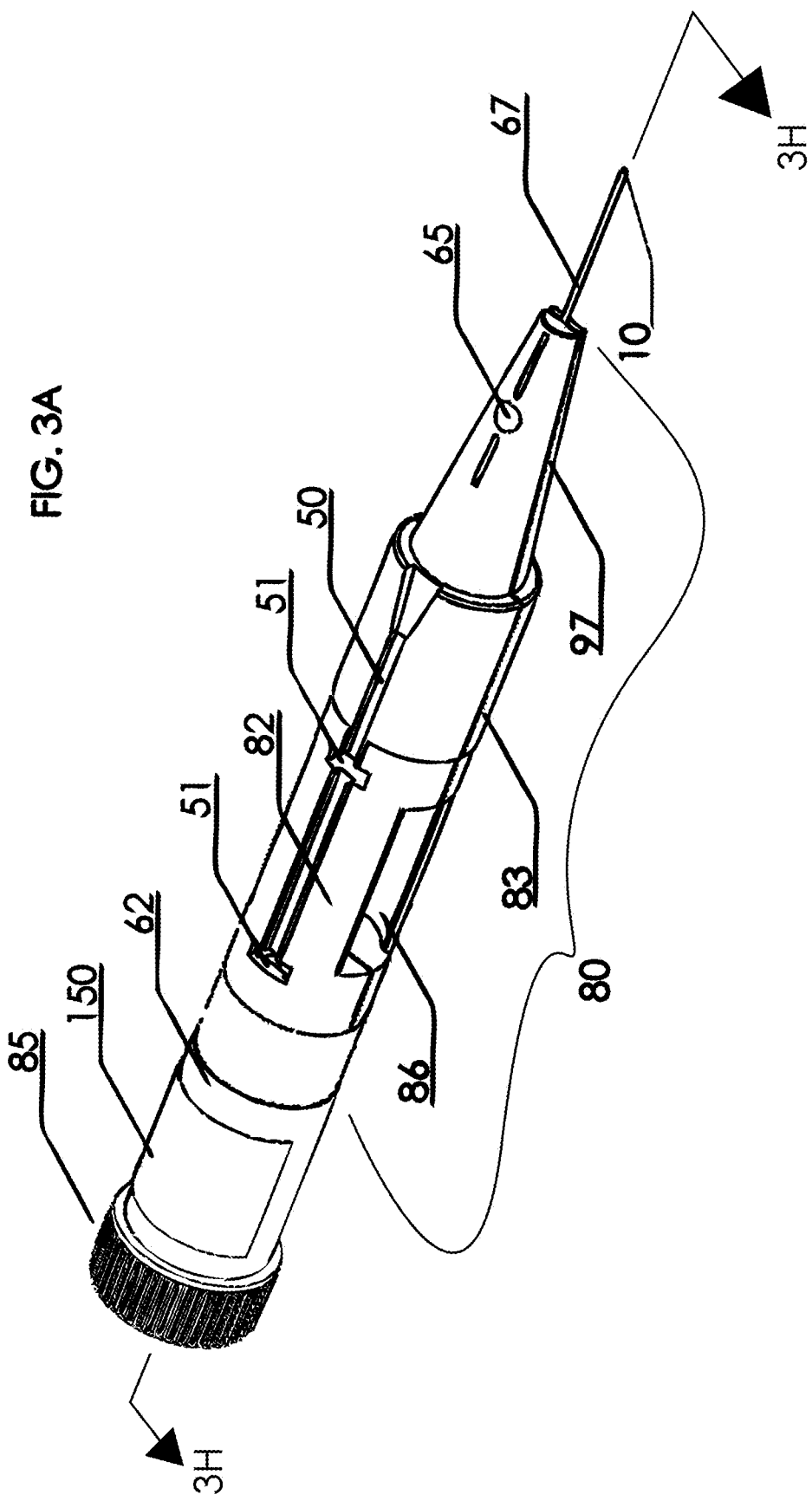
Figure 3C:
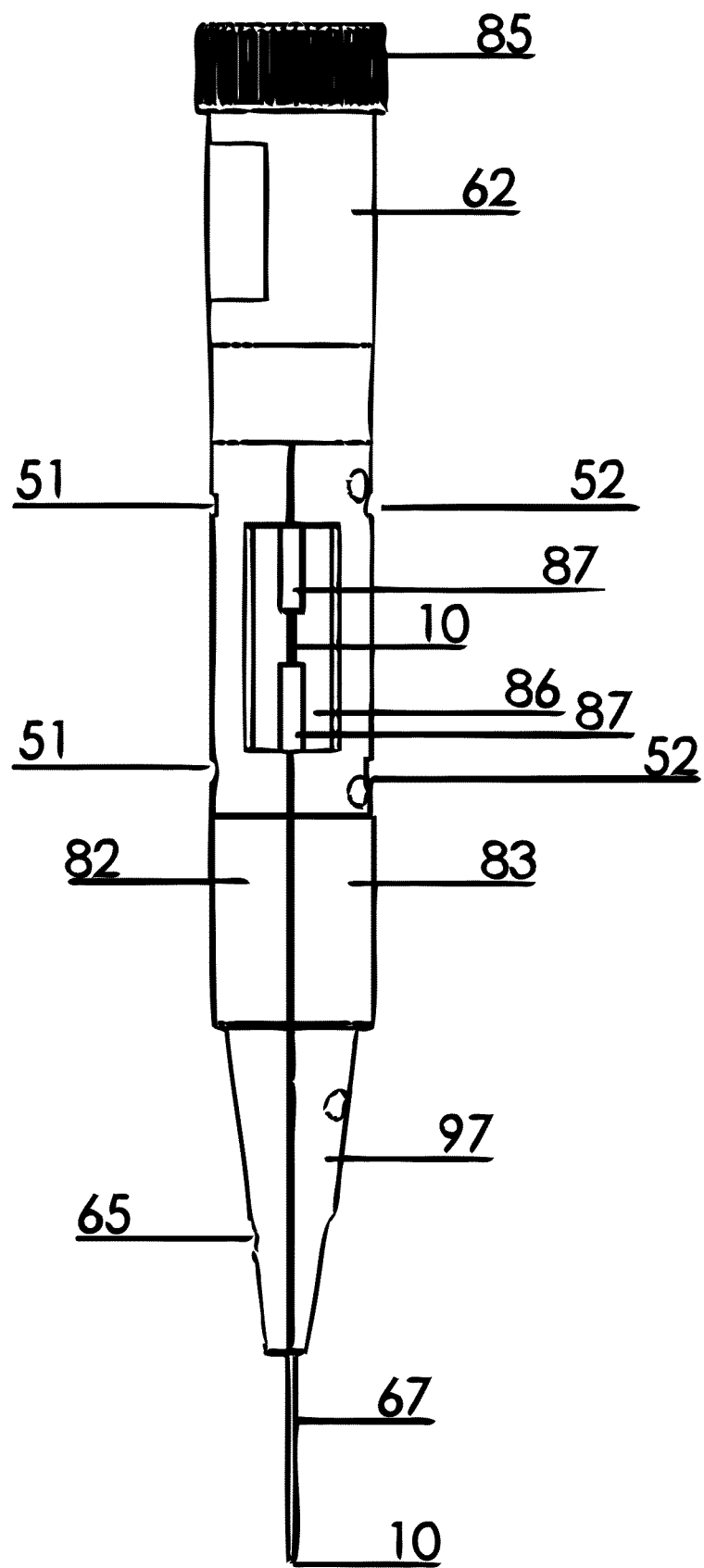
FIGS. 3C to 3G are planar views of different sides and surfaces of the cartridge.
Figure 3D:
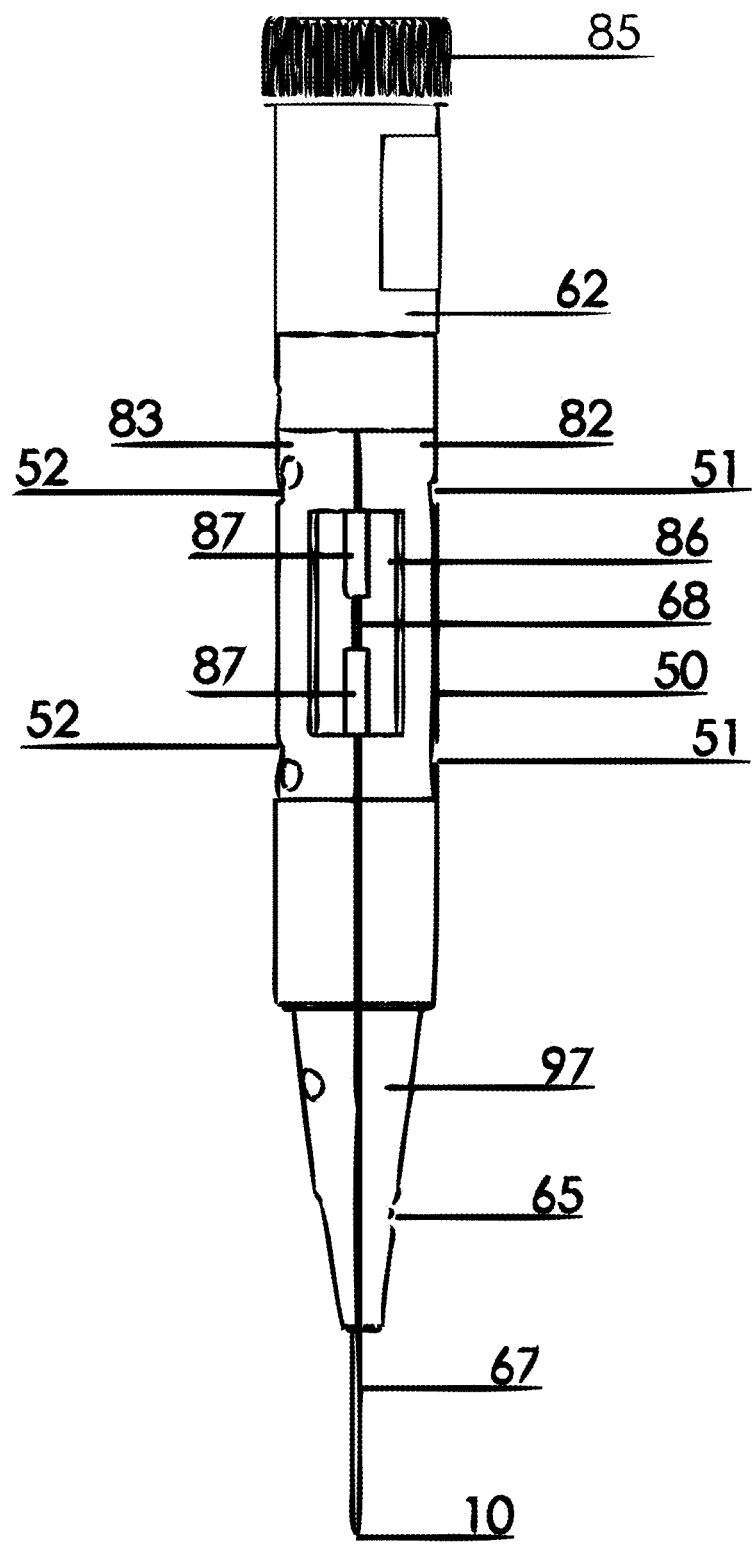
Figure 3E:
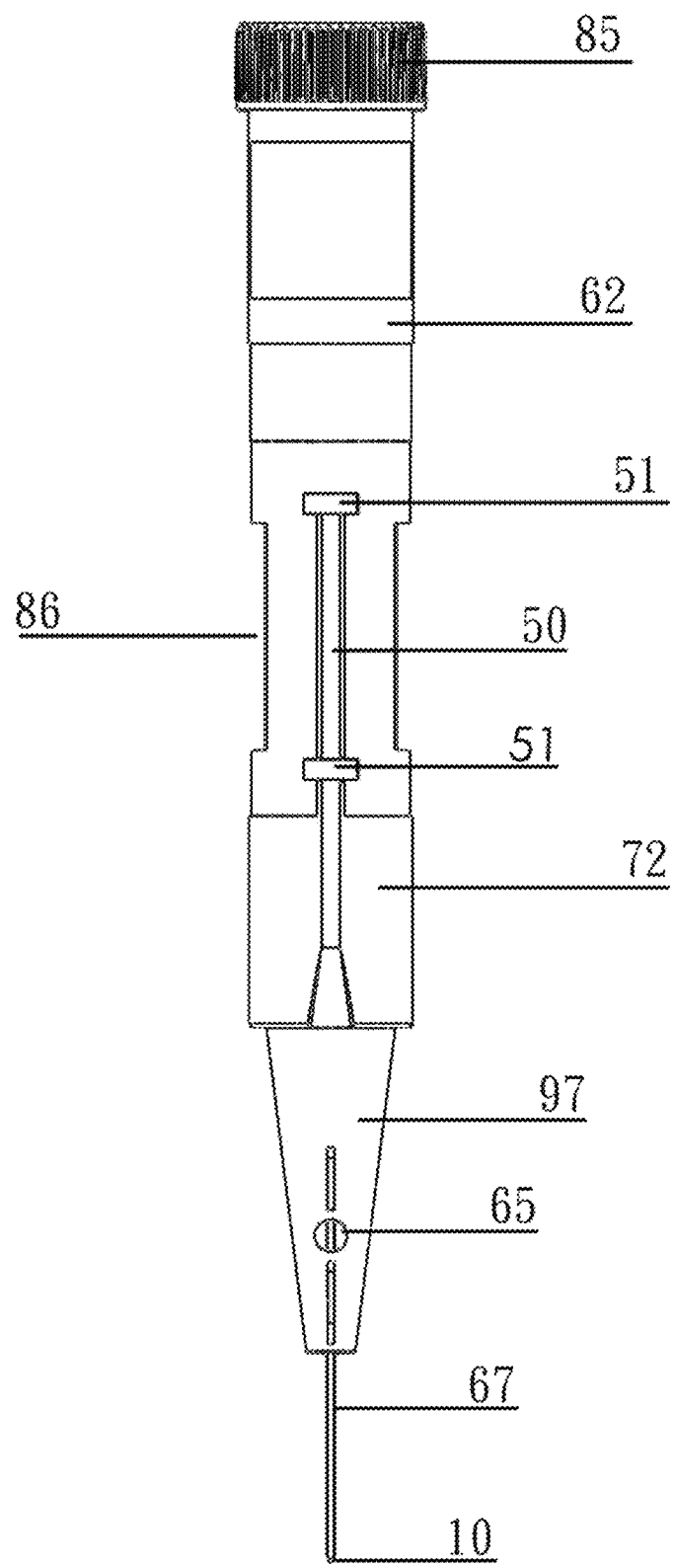
Figure 3F:
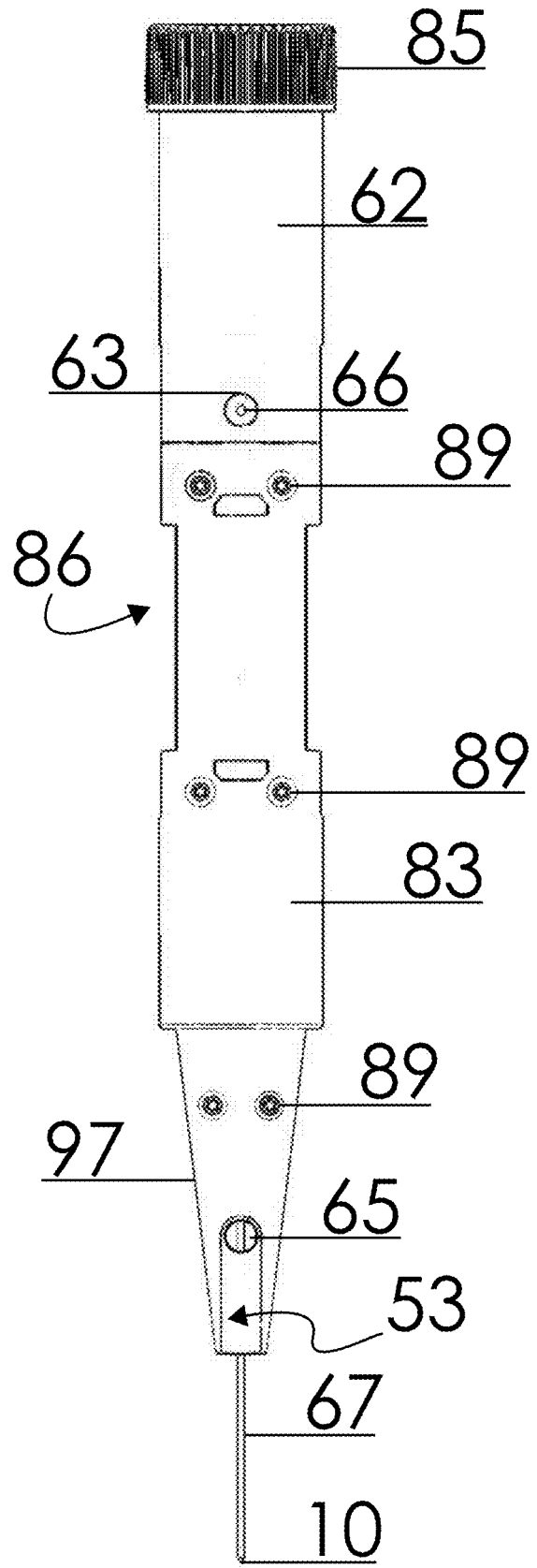
Figure 3G:
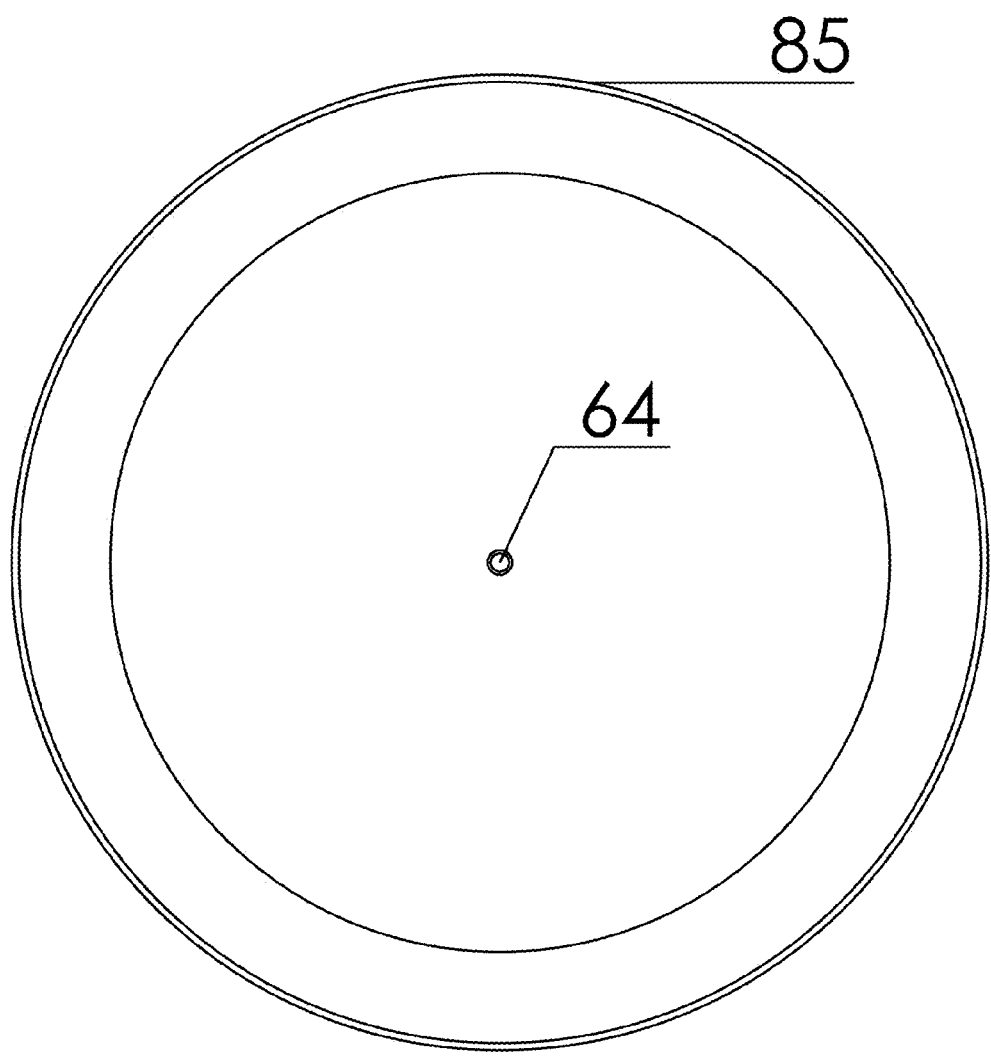
Figure 3H:
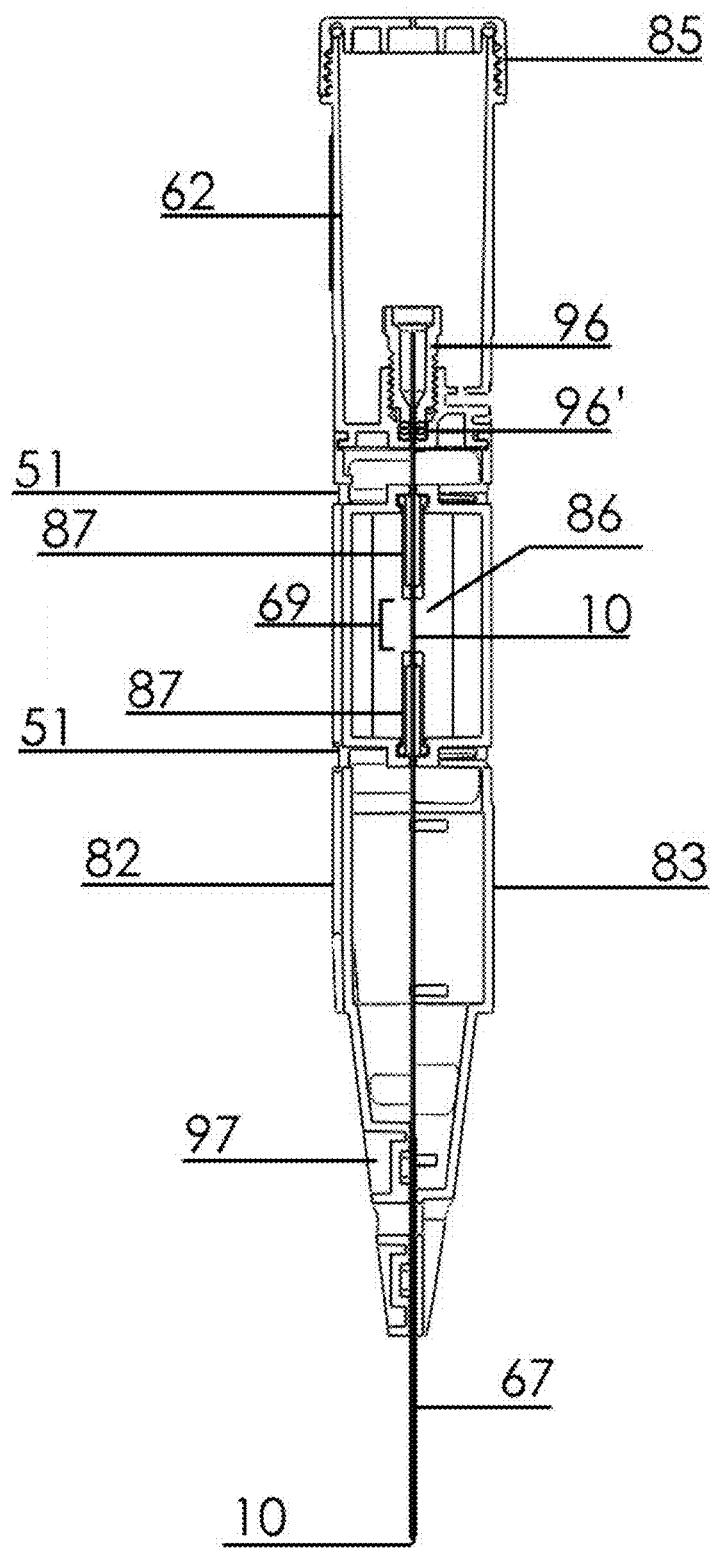
FIG. 3H is a sectional view taken along line 3H-3H in FIG. 3A, illustrating the two half shells attached together.

Referring also to FIG. 3H that is a sectional view of the two half shells attached together, cylindrical sleeves or ferrules 87 upstream and downstream of the detection zone 68 support the capillary column 10 within the body 80 of the cartridge 60 (see also FIG. 4). The capillary column 10 is threaded through the ferrules 87, and one end of the capillary column 10 extends into the reservoir 62 in fluid communication with the buffer contained in the reservoir 62, and the other end extends to depend beyond the lower end of the cartridge body 80. In the illustrated embodiment, to secure the upper end of the capillary column 10 in the reservoir 62, a threaded nipple 96 having a through-hole is threaded into the base of the reservoir 62 and compress against an O-ring seal 96' (see also FIG. 6C). The upper end of the capillary column 10 is inserted through the nipple 96. The threaded nipple 96 provides flexibility in removing the capillary column or accommodating capillary columns of different lengths. Alternatively, instead of using the nipple, the end of the capillary column 10 can be secured to the reservoir 62 by glue or epoxy. The ferrules 87 extend from the recesses 94 into the window 86, but expose the detection zone 68 of the capillary column 10. The two half shells 82 and 83 are assembled together to form the body 80, e.g., by screws 89, or epoxy, or clips. The capillary column 10 is supported coaxially by the ferrules 87, which are supported in the cartridge body 80, wherein each of the ferrules 87 is cantilevered by the cartridge body and having an end extending into the detection window 86, and wherein the detection zone along the capillary column is exposed between the extended ends of the ferrules.

At the lower end of the cartridge 60 is another electrode 67 (cathode). The electrode 67 has contact surface exposed to external through opening 65 at the conical portion 97 of the cartridge body 60 half shells 82 and 83, for coupling to an external high voltage power supply in the CE instrument for electrophoresis when installed inside a CE instrument, such as the embodiment described herein below (see, FIGS. 7 to 9), which is designed to receive the cartridge 60. The lower electrode 67 is configured in the form of metal/conductive sleeve, extending from the lower end of the cartridge 60, and surrounding the side of the depending end of the capillary column 10 completely (e.g., in the form of a co-axial metal tube) or partially (e.g., in the form of a wire mesh, gauze or net, or an open channel having a C-shaped cross-section), with the tip of the capillary column 10 exposed for fluid communication with an external buffer reservoir. The tip of the capillary column 10 may extend beyond the end of the electrode 67, for better access to samples.

To assembly the various components shown in FIG. 3, the bottom rim 88 of the reservoir 62 is placed at the end of the half shells 83, with the flange 92 inserted in the groove 93 on the reservoir 62. The capillary column 10 is threaded through the ferrules 87, and one end is threaded into the bottom electrode 67. The other end of the capillary column 10 is inserted into the bottom opening 91 on the reservoir 62, through the nipple 96. The nipple 96 is tightened onto the base of the reservoir 62, compressing the O-ring 96' to provide a seal against the body of the capillary column 10. The far ends of the ferrules 87 are inserted in recesses 94 on the half shell 83. The lower electrode 67 is positioned in the groove 95 provided on the inside the conical portion 97 of the half shell 83, with the end extending beyond the conical portion 97. A drop of glue may be provided to secure the electrode 67 in the groove 95. The other half shell 82 is placed over the half shell 83 and attached by suitable fasteners, such as rivets or screws 89 as shown. The reservoir 62 is filled with the desired separation support medium (buffer) and capped. The fully assembled cartridge 60 may be tested and labeled.

An electronic label, such as an RFID label 150 may be imbedded or attached to the cartridge 60 (e.g., at the outside cylindrical surface of the reservoir 62), to provide a means of identification of the particular configuration of the cartridge (e.g., buffer medium, capillary size, coating and length). The RFID label may also include the pre-set limit on the number of runs and type of cartridge with expiration date. After assembling the cartridge 60, the RFID label is provided with the initial configuration parameters. The RFID may be re-recordable and updated with information to track usage of the cartridge (e.g., the number of runs and the conditions and/or parameters of the runs (e.g., applied voltage, duration, sample), the number of time the cartridge has been reconditioned, etc.), so that the history of the cartridge can be easy determined (e.g., by the CE instrument discussed below or by a separate reader). The end of the useful life of each cartridge can also be determined from the RFID label. Alternatively, a static label, such as a bar code label may be provided.

As will be explained in greater detail below, in electrophoresis operation as installed in the CE instrument, the end of lower electrode 67 along with the open end of the capillary column 10 are dipped into an external buffer reservoir. To conduct electrophoresis, high voltage is supplied to the electrode 66 in the buffer reservoir 62 and the electrode 67 dipped in the external reservoir, to provide a high voltage circuit across the buffer to complete the electrophoresis path in the capillary column 10. The electrode 67 also provides protection to prevent breakage of the depending end of the capillary column 10.

The cartridge does not require detection optics to be integrated into the cartridge, and the separation channel does not require fine alignment with respect to the detection zones. Specifically in the illustrated embodiment, the cartridge does not include integrated detection optics. Referring also to the schematic sectional view of FIG. 4 taken along an axial plane of the cartridge 60, the internal of the cartridge 60 having a cavity 69 (defined by the detection window 86) surrounding the region of the detection zone 68 is shown (the detection zone 68 corresponds to the detection zone 32 shown in FIG. 1). Sleeves or ferrules 68 upstream and downstream of the detection zone 68 support the capillary column 10 in the body of the cartridge 60. External excitation fiber 34 and emission fiber 36 supported in the CE instrument are aligned with the detection zone 68 through the detection window 86 defined in the separation channel/column 10. In the illustrated embodiment that will be further discuss below, the excitation fiber 34 and emission fiber 36 are supported by the fork assembly in the CE instrument (see FIG. 10, for example). The axes of the fibers 34 and 36 and the capillary column 10 are coplanar. The ball ends of the fibers 34 and 36 are in proximity to but not touching the capillary column 10. In other words, the optical fiber has a terminating integral ball-end structure that is spaced apart from exterior of the separation channel, wherein the ball-end structures do not touch exterior of the separation channel.

In another aspect of the present invention, the chemistry of the buffer medium and the characteristics of the capillaries (e.g., capillary size, coating and length) are defined for each cartridge. Different cartridges can be easily interchanged for use in the CE instrument discussed below to suit the particular sample based separation. The cartridges may be replaced, reconditioned (e.g., with fresh buffer, seals, new capillary column and/or electrodes, etc.), recycled, or disposed.

The cartridge in accordance with the present invention can be manufactured with relatively low cost. The body of the cartridge can be made of injection molded plastic (e.g., PVC, polyurethane, polycarbonate, acytal, etc. The electrodes can be made of stainless steel. The ferrules could be made of injected molded plastic material or aluminum or glass machined parts.

In the illustrated embodiment, the overall size of the cartridge 60 is less than 25 cm in length (e.g., about 18 to 20 cm), and less than 5 cm in diameter (e.g., 2 to 3 cm). The length of capillary column 10 that can be accommodated in the cartridge 60 is less than 20 cm (e.g., about 15 to 17 cm). The capacity of the reservoir 62 is less than 50 cc (e.g., about 15 to 30 cc).

CE Instrument

Figure 7:
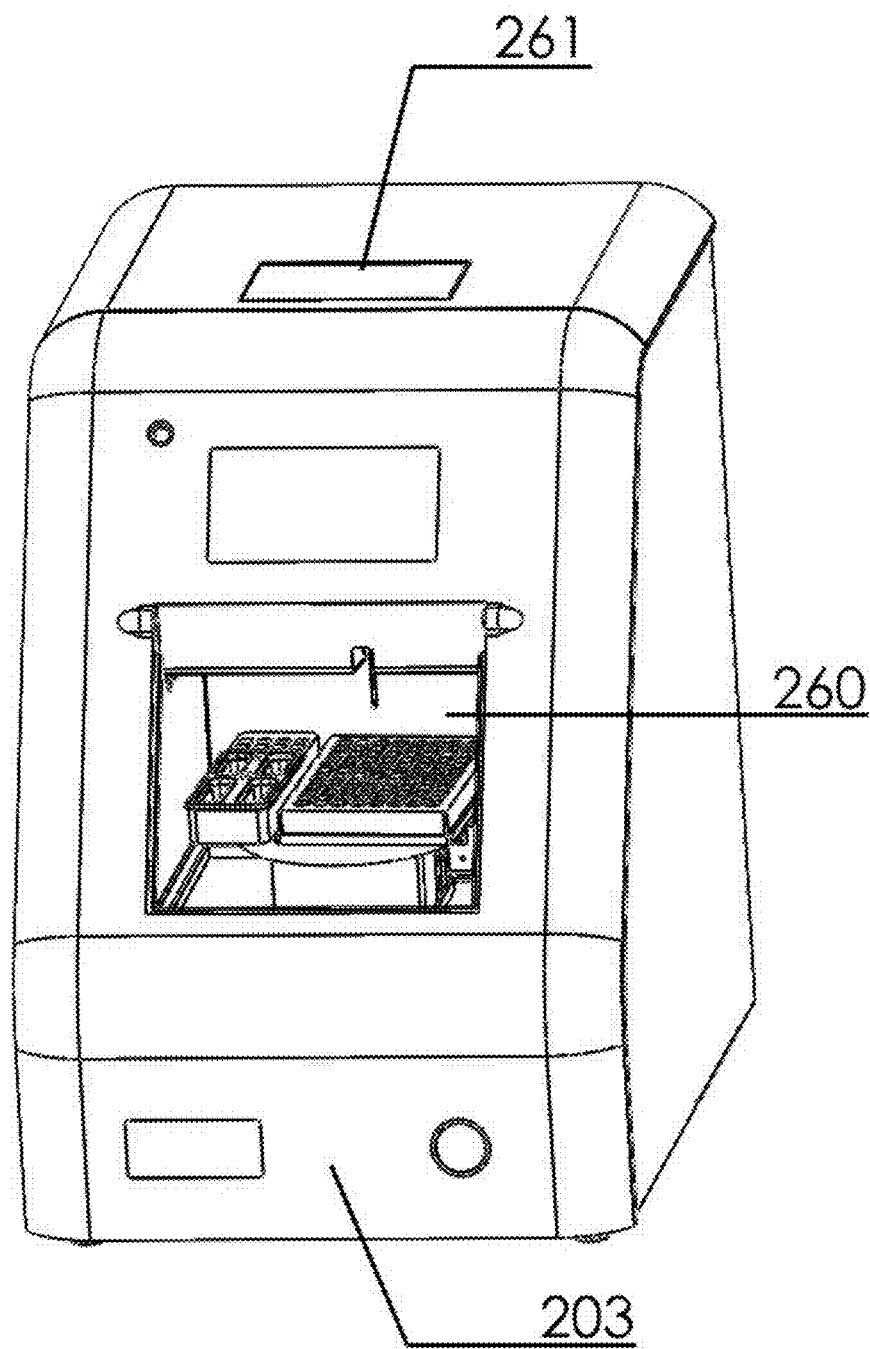
FIG. 7 illustrates the external view of a CE instrument, in accordance with one embodiment of the present invention.
Figure 8:
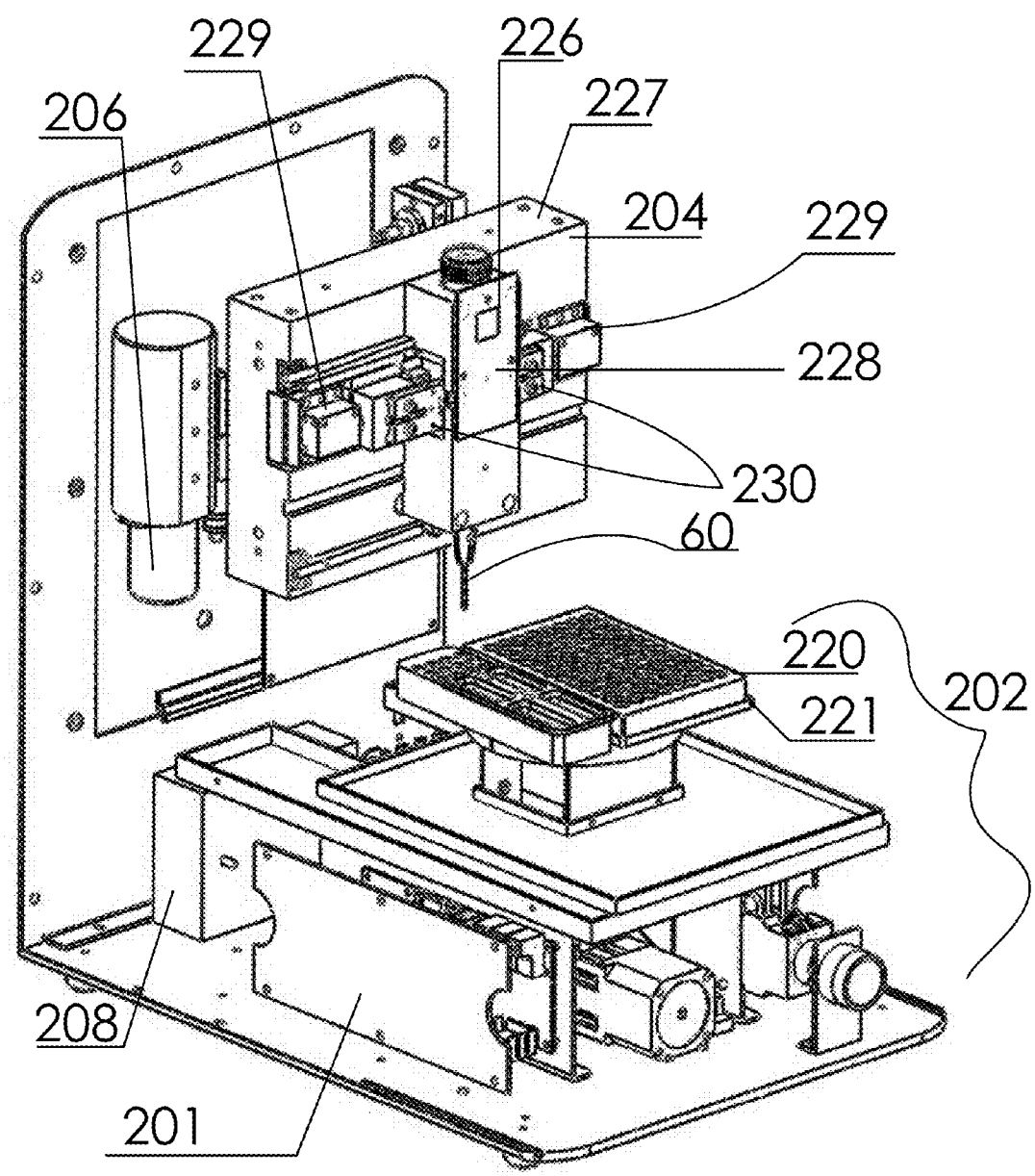
FIG. 8 illustrates the internal view of the CE instrument of FIG. 7, in accordance with one embodiment of the present invention.
Figure 9:
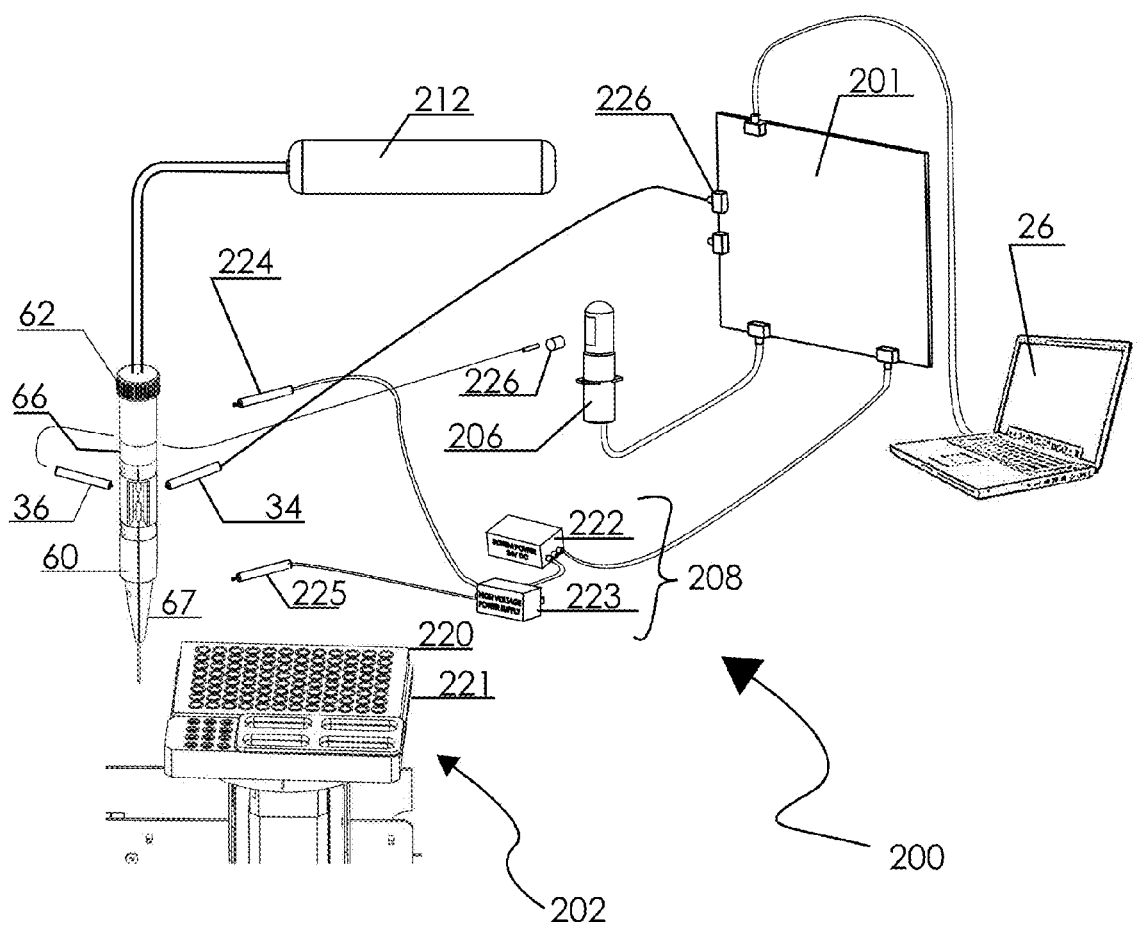
FIG. 9 is a schematic view illustrating the components of the CE instrument of FIGS. 7 and 8, in accordance with one embodiment of the present invention.

FIG. 7 illustrates that external view of the CE instrument 200 in accordance with one embodiment of the present invention. FIG. 8 illustrates that internal view of the CE instrument 200 with the front and side housing 203 removed, in accordance with one embodiment of the present invention. FIG. 9 is a schematic view illustrating the components of the CE instrument 200, some of which reside within the instrument housing, and some outside of the housing. The CE instrument 200 comprises a system board 201, operatively coupled to a sample transport mechanism 202, a cartridge interface mechanism 204, an optical signal detector such as a photomultiplier tube (PMT) 206, a power supply 208 (which includes a high voltage power supply 223, and may further include a system power supply 222; the power supply 222 may reside outside of the CE instrument 200), detection optics 210, and a pressurized gas source 212 (which may reside outside the CE instrument 200, but connected to a port in the instrument housing).

A controller 26 is provided for user interface and programming of experiment/test settings and parameters. The controller includes the necessary application software routines, which may also include data reduction applications. The controller 26 may be an integral part of the instrument 200 (e.g., as part of the system board 201, with application routines coded in ASICs), or it may be a separate unit coupled/interfaced to the CE instrument 200. In the illustrated embodiment, the controller is external to the housing of the CE instrument 200, in the form of a desktop computer or notebook computer, which is coupled to the CE instrument 200 via the system board 201 via a USB interface. The external controller 26 may include mass storage devices, display, keyboard, etc., or some of these user interface components may be configured integral to the CE instrument (e.g., a display and a keyboard on the front housing). Alternatively, the system board 201 may be incorporated as part of the external controller 26, without departing from the scope and spirit of the present invention.

The system board 201 includes the necessary electronics to drive the various components in the CE instrument, e.g., the movements of the transport mechanism 202, the output of the power supply 208, the PMT 206, the valve release of the pressurized gas 212, the movements of the cartridge interface 204, an RFID transmitter/reader, etc. It is noted that the system board 201 is schematically represented in the figures. It may include other electronic boards for controlling specific components (e.g., electronic board for controlling motors in the sample transport mechanism 202), or these other boards may be separate from and in communication with the system board 201 to perform the intended function. The exact electronic board configuration is not critical to the present invention, and it is well within the knowledge of one skill in the art to configured the boards to achieve the desired functions and features disclosed herein.

The sample transport mechanism 202 includes a table 221 supporting a sample and buffer tray 220 having multiple wells (e.g., a standard 96-well titer plate, and larger wells for buffer, cleaning solutions and waste collection) to move with three degrees of freedom. The multiple wells may include wells containing cleaning solutions and samples and also for waste collection. It is noted that in the figures, X, Y and Z are orthogonal axes. Y is the vertical axis; X is in a horizontal direction across the instrument (parallel to the rear of the instrument); and Z is in a horizontal direction into and out of the instrument. The table 221 is controlled by the transport mechanism 202 to move up and down, and to move within a plane in a straight line and rotate within the plane. That is, the table 221 moves in a single horizontal direction (Z-direction), and in a vertical (Y-direction), and rotation about the vertical axis (Y-axis). The combination of rotation and translation motions would be able to place any of the multiple wells in the tray 220 for access by the tip of the depending capillary column 60. The front panel 203 of the instrument housing includes an opening with a door 260 to allow user access to place and remove the tray 220.

The pressurized gas source 212 (e.g., pressurized N2) may be a gas cartridge installed within the housing of the CE instrument, or may be an external source providing pressurized gas to the CE instrument via a gas connection port at the instrument housing (in which case, the pressurized gas source would be the gas connection port to the external gas source). The pressured gas is fed to the reservoir 62 in the cartridge 60 via appropriate gas tubing and valves (which is operatively coupled to the system board 201).

The power supply 208 includes a system DC power supply 222 (e.g., 24 VDC from external AC power) coupled to the system board 201, and a variable high voltage power supply 223 providing the necessary high voltage to electrode contacts/probes 224 and 225, for electrical contact with electrodes 66 and 67 in the cartridge 60 for carrying out electrophoresis therein. Alternatively, instead of using an internal 24 VDC power supply with external AC power, the CE instrument 200 may use an external 24 VDC power supply, which makes the instrument simpler and safer to use without the internal AC to DC conversion. This would also allow for battery operation for field portability and operations. The contact probes 224 and 225 may be actuated pneumatically (e.g., by regulating pressurized gas from the gas source 212, or electromechanically, to contact against the exposed surfaces of the electrodes 66 and 67, or the contract probes 224 and 225 may be simply spring loaded to bias against the exposed surfaces of the electrodes 66 and 67.

The excitation fiber 34 is optically coupled to a light source in the form of an LED 226, which may be part of the system board 201. The emission fiber 36 is optically coupled to the PMT 206 via appropriate optical filters 226. The electrical output of the PMT 206 is coupled to the system board 201.

The cartridge interface mechanism 204 is supported on the chassis of the instrument, and is configured to receive the cartridge 60, and index its location positively and accurately with respect to the detection optics 210. A door 261 (FIG. 7) is provided at the top panel of the instrument housing. The cartridge interface mechanism 204 includes a base 227 supporting a receiver block 228 having a cylindrical opening sized and configured to receive the cartridge 60 as shown. In this illustrated embodiment, the cartridge 60 is support by the receiver block 22 in a vertical orientation, with its longitudinal axis substantially vertical with respect to the horizontal plane of the tray 220. It is within the scope of the present invention to have the cartridge supported with its longitudinal axis horizontal with respect to reagent/sample containers. The receiver block 228 includes indexing keys (not shown) that complements the alignment slot 50 and indexing recesses 51 provided on the half shell 82 of the cartridge 60 (see, e.g., FIG. 3A), and indexing recesses 52 and 53 provided on the half shelf 83 of the cartridge 60 (see, e.g., FIG. 3B). The alignment slot 50 and indexing recesses 51 provide guides to facilitate positive and accurate positioning and alignment of the detection window 86 in the cartridge 60 with respect to the fork assemblies 230 discussed below, when the cartridge 60 is properly inserted into the CE instrument. One of more of the indexing keys may be provided with a safety interlocking feature, which is engaged to prevent the cartridge 60 from being accidentally removed from the receiver block 228 during electrophoresis operations. The safety interlock feature could also include the front door 260 for tray 220 and top door 261 for insertion of the cartridge 60 (FIG. 7), to prevent user accidentally opening these doors during electrophoresis operations. The safety interlock (not shown) will only be released upon execution of termination sequence for an electrophoresis run (e.g., shutting down high voltage supply, and outward movement of the fork assemblies 230 described below). The receiver block 228 also includes an RFID reader/transmitter 266 (e.g., on the outside of the receiver block 228) for communicating with the RFID label 150 on the capillary column 10.

Figure 6C:
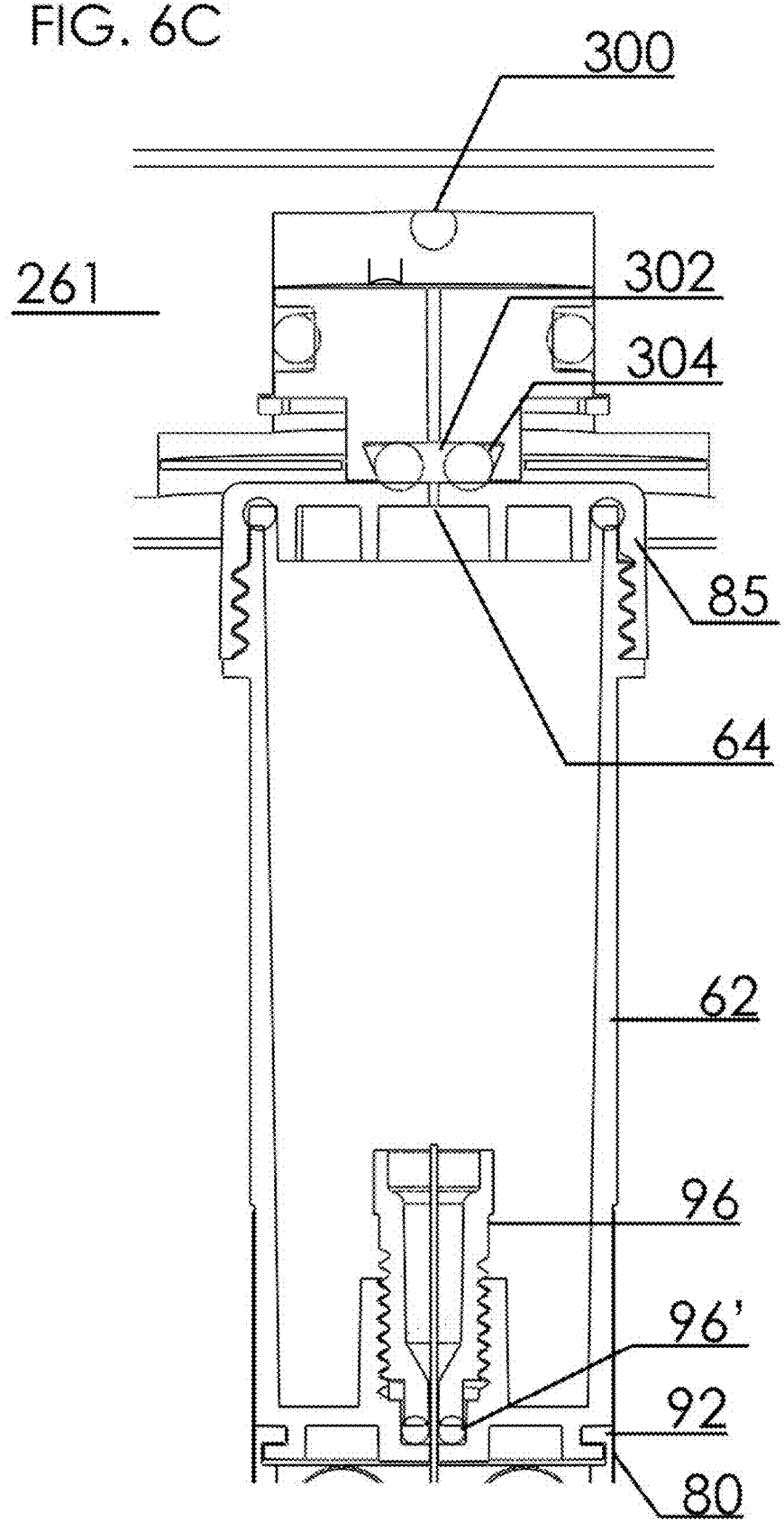
FIG. 6C is a sectional view illustrating the instrument pressure port region above the cap of the reservoir.

In the illustrated embodiment, the pressurized gas is delivered from outside the instrument to a valve (not shown) in the instrument. Referring to FIG. 6C, pressurized air delivery tube 300 is coupled from the valve to an air outlet 302 at the underside of the top door 261, at a location above the cap 85 of the cartridge reservoir 62. The air outlet 302 includes an O-ring 304 that presses onto the top of the cap 85 of the cartridge reservoir 62 when the door 261 is closed properly (e.g., with safety interlock engaged). This provides a sealed interface to deliver the pressurized gas to the port 64 in the reservoir cap 85.

Figure 10:
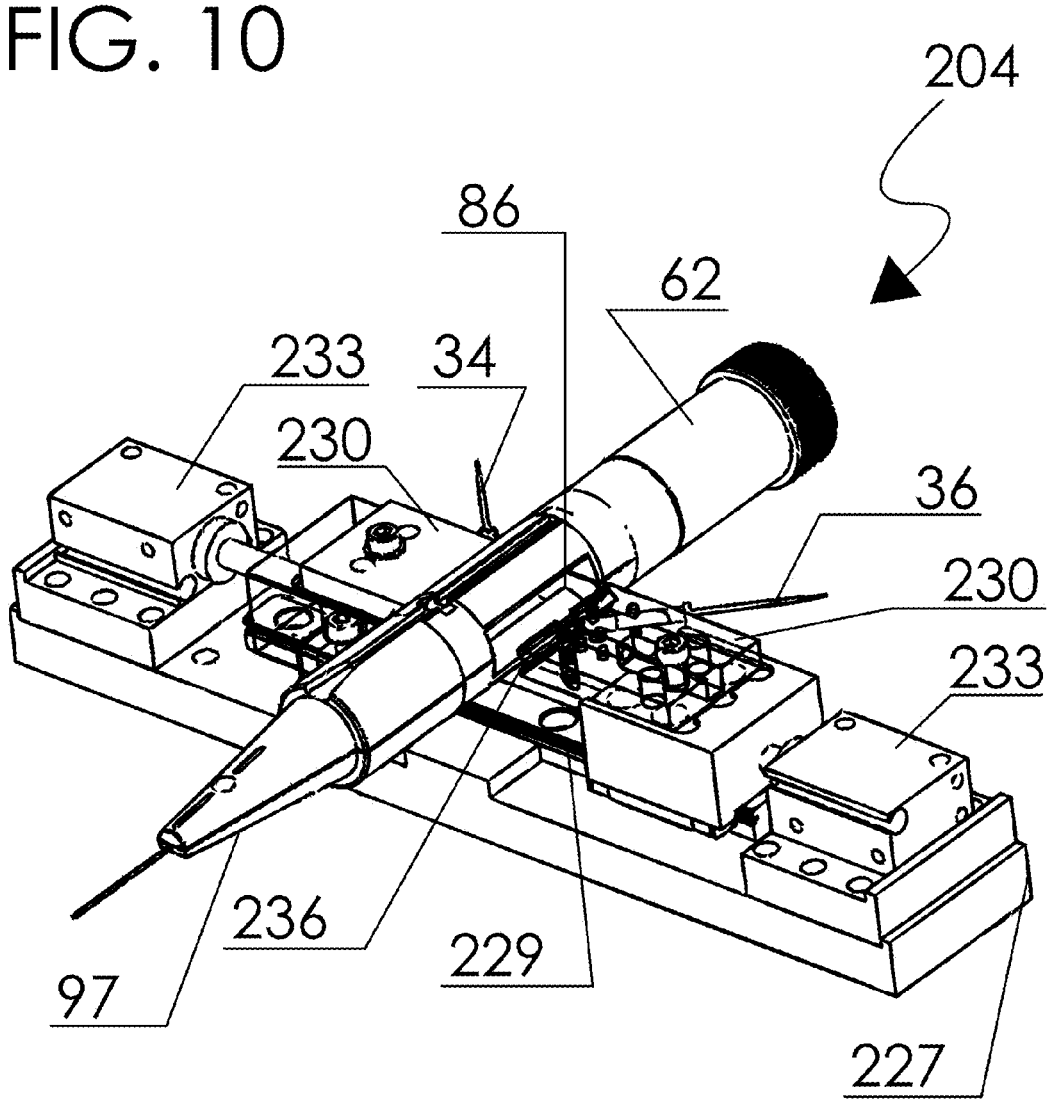
FIGS. 10-12 illustrates the fork assembly in accordance with one embodiment of the present invention.
Figure 11:
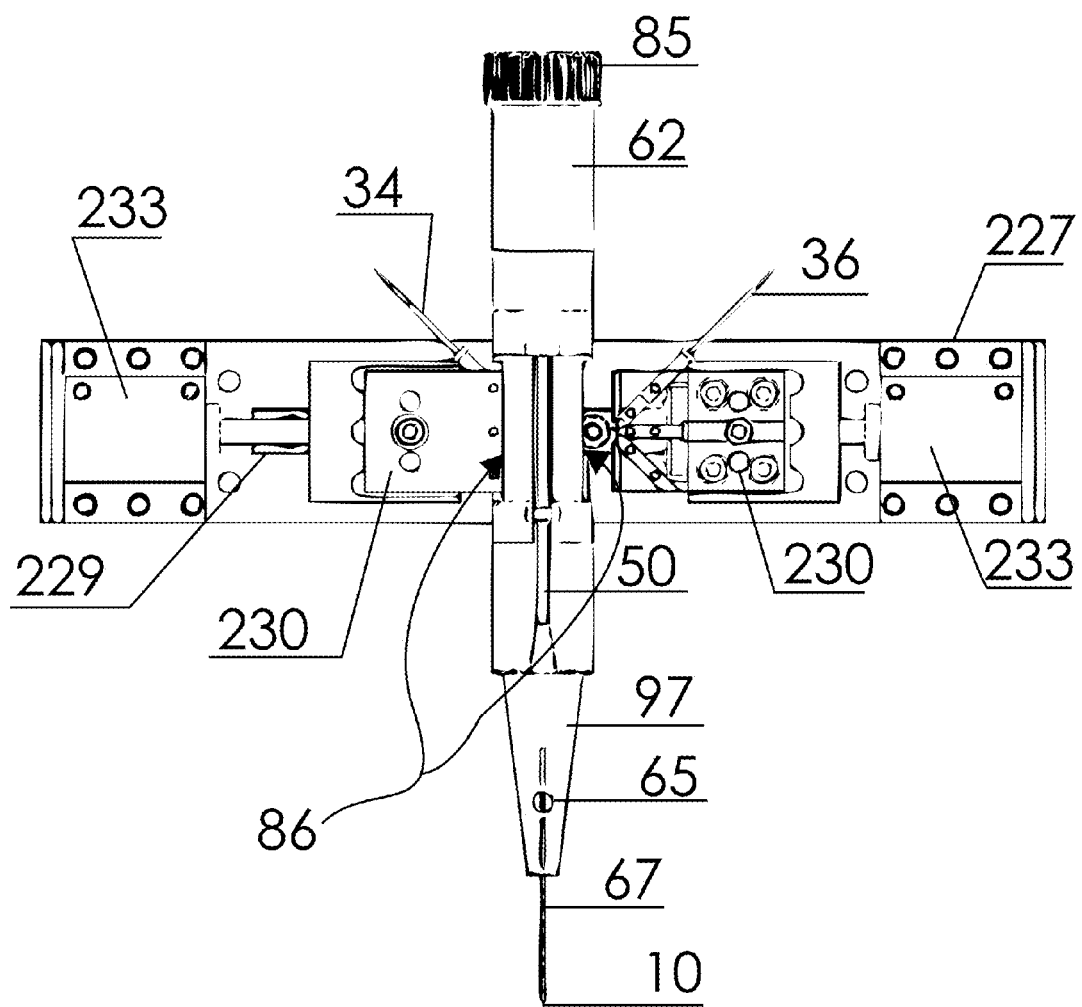
Figure 12:
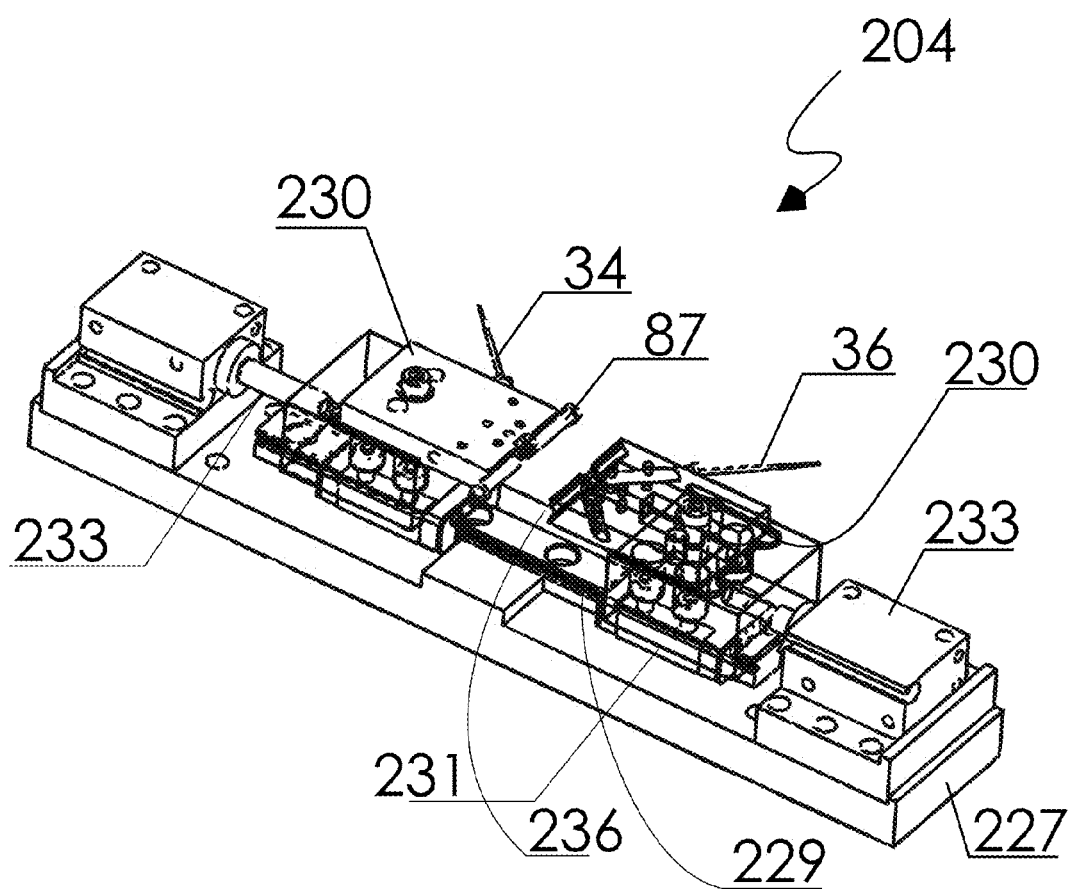

The base 227 further supports tracks 229 for movement of fork assemblies 230. Referring also to FIGS. 10 to 12, the fork assemblies 230 are attached to slides 231, which are actuated to be slidable along the tracks 229 towards and away from each other (i.e., in the X-direction in the drawings). In other words, in the illustrated embodiment, the fork assemblies are supported to slide along a same axis. The excitation fiber 34 and emission fiber 36 are each supported on a fork assembly 230. The fork assemblies 230 are configured to position the ball shaped ends of the excitation fiber 34 and the emission fiber 36 in proximity to the detection zone 68 of the capillary column 10 for detection of separated sample analytes. Movements of the fork assemblies 230 may be implemented by pneumatic or electromagnetic actuation. In the illustrated embodiment, the fork assemblies 230 are moved by pneumatic pistons 233, which may make use of the supply of pressurized gas 212 regulated by appropriate valve(s) (not shown) controlled by the system board 201.

The cartridge 60 is positioned with respect to the fork assemblies 230 in a manner such that the fork assemblies 230 are positioned on opposite lateral sides of the cartridge 60, wherein the fork assemblies move between a first position in which the first and second fork assemblies do not extend into the detection window defined in the cartridge, and a second position in which the first and second fork assemblies extend into the detection window defined in the cartridge. The fork assemblies 230 essentially move between a first position at which the fork assemblies are apart to allow the cartridge 60 to be inserted between the fork assemblies 230, to a second position at which the fork assemblies are pressing against the ferrules 87 (interlocked) in the detection window 86 in the cartridge 60.

The extended portion of the fork assemblies 230 are provided with a complementary surface that facilitates alignment of the extended surface against the ferrule 87, e.g., a grooved or concave surface 236 to complement the cylindrical body of the ferrules 87. FIG. 12 is a simplified view that illustrates the fork assembly 230 (the one having the excitation fiber 34) pressed against the ferrules 87 (the rest of the cartridge 60 is not shown in this view). At the second position, the concave surfaces 236 extend into the detection window 86 in the cartridge 60, as illustrated in FIG. 11 (see also FIG. 4). In this position, an optical fiber supported on one fork assembly delivers radiation to the capillary column, and another optical fiber supported on another fork assembly collects radiation from the detection zone. In the particular illustrated embodiment, radiation induced fluorescence detection scheme is implemented, but other types of optical detection schemes may be implemented instead without departing from the scope and spirit of the present invention. Both fork assemblies 230 may be controlled to move together to press against the ferrules 87 at about the same time, or move separately to press against the ferrules 87 in sequence. In the illustrated embodiment, the ferrules 87 provide a stop against the extended surfaces of the fork assemblies 230, so that the terminating integral ball-ends of the optical fibers do not touch the exterior surface of the capillary column, but are spaced apart from the exterior surface of the capillary cartridge at a predetermined distance, which can be repetitively maintained when the fork assemblies are actuated between the first and second positions described above.

While the illustrated embodiment shows the optical fibers oriented in a V-configuration, the optical fibers may be configured in a straight or in-line fashion (e.g., for absorbance type detection scheme), or with one or both optical fibers configured with axis perpendicular to the axis of the capillary column. Further, only one fork assembly may be used, with both radiation delivering fiber and radiation collection fiber on the same fork assembly.

The system board 201 controls various functions of the CE instrument 200, including positioning the sample and buffer tray 220 with respect to the cartridge 60 held in the receiver block 228, and above described functions of the cartridge interface mechanism 204, and other functions, such as detecting end of a run and release of safety lock to release the cartridge 60 from the receiver block 228.

In one embodiment, the variable high voltage power supply (e.g., EMCO, Sutter Creek, Calif.) (0V to 20 KV is used to deliver electrical field (e.g., 4 to 13 KV) to the capillary for the electro kinetic injection and separations of bio-molecules. Multi-mode optical fibers (100 µm-to-500 µm) deliver the excitation light (from an LED: 200-700 nm) and collect the emission signal (fluorescence light) and transfer it to PMT for data analysis. The PMT module may have a built-in emission filter (e.g., Long Pass Filter=520-650 nm or Band-Pass Filter at 530 nm or 620 nm) to improve detection sensitivity. Specifically in the illustrated example, an excitation LED (460 to 490 nm or 500 to 550 nm) having broad band light energy (FWHM=50 nm) and 100 degrees of viewing angle is coupled to the large core excitation fiber (100-1000 micron) at the flat end (polished or cleaved end). A line filter (FWHM=2-50 nm Band Pass line filter) in placed in front of the LED before coupling the light into the 200 micron diameter core with 350 diameter micron ball-ended excitation fiber to reduce background noise. The micro-ball lens end of the fiber is produced by fusion splicing (high voltage heat melting) with a well controlled ball diameter to create a well defined exit NA and spot size for coupling the excitation radiation energy into the inner diameter (the separation channel) of the capillary column. The fluorescence emission signal produced by the separated analytes are then collected at the detection zone of the capillary channel using a similar ball-ended fiber (larger core fiber with 500 micron diameter ball) and is relayed to an external detector module (shown in FIG. 9, which may be a PMT or SiPMT or CCD) with a build in emission filter (Band Pass Filter=520 nm) for FITC dye related applications, for example.

System Operation for Electrophoresis:

To conduct a desired electrophoresis run, a user presets the appropriate parameters using the controller 26. A cartridge 60, having the appropriate separation support medium (buffer) and a capillary column 10 having the desired size and coating, is inserted into the receiver block 228. The controller 26 in association with the system board 201 takes over control of the CE instrument 200, to undertake the tasks described below.

The cartridge is "locked" in the receiver block 228 upon proper insertion, with the detection window appropriately positioned with respect to the fork assemblies 230. Pressurized gas is readied from source 212, when the top door 261 is closed to press the O-ring of the air outlet against the top of the cap 85 of the cartridge reservoir 62 to access the port 64 on the cartridge reservoir 62. The electrical contact probes 224 and 225 are pressed against the electrodes 66 and 67. The fork assemblies 230 are moved to mate against the ferrules 87 in the detection window 86.

By a combination of X, Y and Z-directions, the sample transport mechanism positions the appropriate wells in the sample and buffer tray 220 with respect to the depending tip of the capillary column 10. If necessary, the separation buffer that is present in the capillary column 10 is initially purged by application of pressurized gas into the cartridge reservoir 62 (the tray 220 may be moved to position a specific well for collecting waste from the capillary column), and/or fresh separation buffer from the reservoir is caused to fill the separation channel.

The test sample that is placed in a well on the tray 220 is positioned to submerge the depending tip of the capillary column 10 and the end of electrode 67. The sample is introduced into the separation capillary column 10 by electro kinetic injection (appropriate high voltage applied for a defined period of time, e.g., less than 60 seconds, e.g., 5 to 10 seconds), a procedure well known to one skill in the art.

A buffer reservoir in the tray 220 is then positioned to submerge the tip of the capillary column 10 and the end of electrode 67. Electrophoresis is carried out by application of high voltage at an appropriate level for a defined period of time for the particular sample and separation buffer medium. During the run, data corresponding to radiation-induced fluorescence is collected via the PMT 206. The data is stored in an electronic file. At the end of the run, the tray 220 is lowered.

If no further runs, the cartridge 60 may be removed by executing a preset release procedure, including releasing the pressurized gas supply, moving the fork assemblies 230 away from the cartridge 60 (as described above), disengaging the electrodes 66 and 67 by the contact probes 224 and 225 (if they are actuable), and releasing the lock on the cartridge 60. The cartridge 60 can thus be removed, and replaced with another cartridge for a next run at a desired time.

If further runs are desired for same or additional samples, the old buffer (e.g., gel buffer) from the previous run is purged into the waste well from the capillary column 60 by pressuring the reservoir to refill the capillaries with fresh buffer. The tray 220 is positioned so that the tip of the capillary column 60 is cleaned with cleaning solution (in a well), before another sample is loaded into the capillary column 60 and electrophoresis run conducted as described earlier.

It is noted that because the sample analytes that flowed to the buffer reservoir 62 at the exit of the capillary column are in such small amount and volume concentration compared to the volume of the reservoir, and that the analytes are expected to be mixed within the gel reservoir, there will only be a negligible trace of analytes from past runs in the reservoir, and that will be evenly distributed in the gel that refills the capillary column for subsequent runs. Any noise from this negligible trace would be relatively small background noise that can be easily removed from the detected signal in the data analysis.

If no further runs, the cartridge 60 may be removed by executing a preset release procedure, including releasing the pressurized gas supply, moving the fork assemblies 230 away from the cartridge 60 (as described above), disengaging the electrodes 66 and 67 by the contact probes 225 and 225 (if they are actuable), and releasing the lock on the cartridge 60. The cartridge 60 can thus be removed, and replaced with another cartridge for a next run at a desired time.

The above-mentioned sequence of process may be programmed as one of the automated functions of the controller 26.

Figures 13A, 13B:
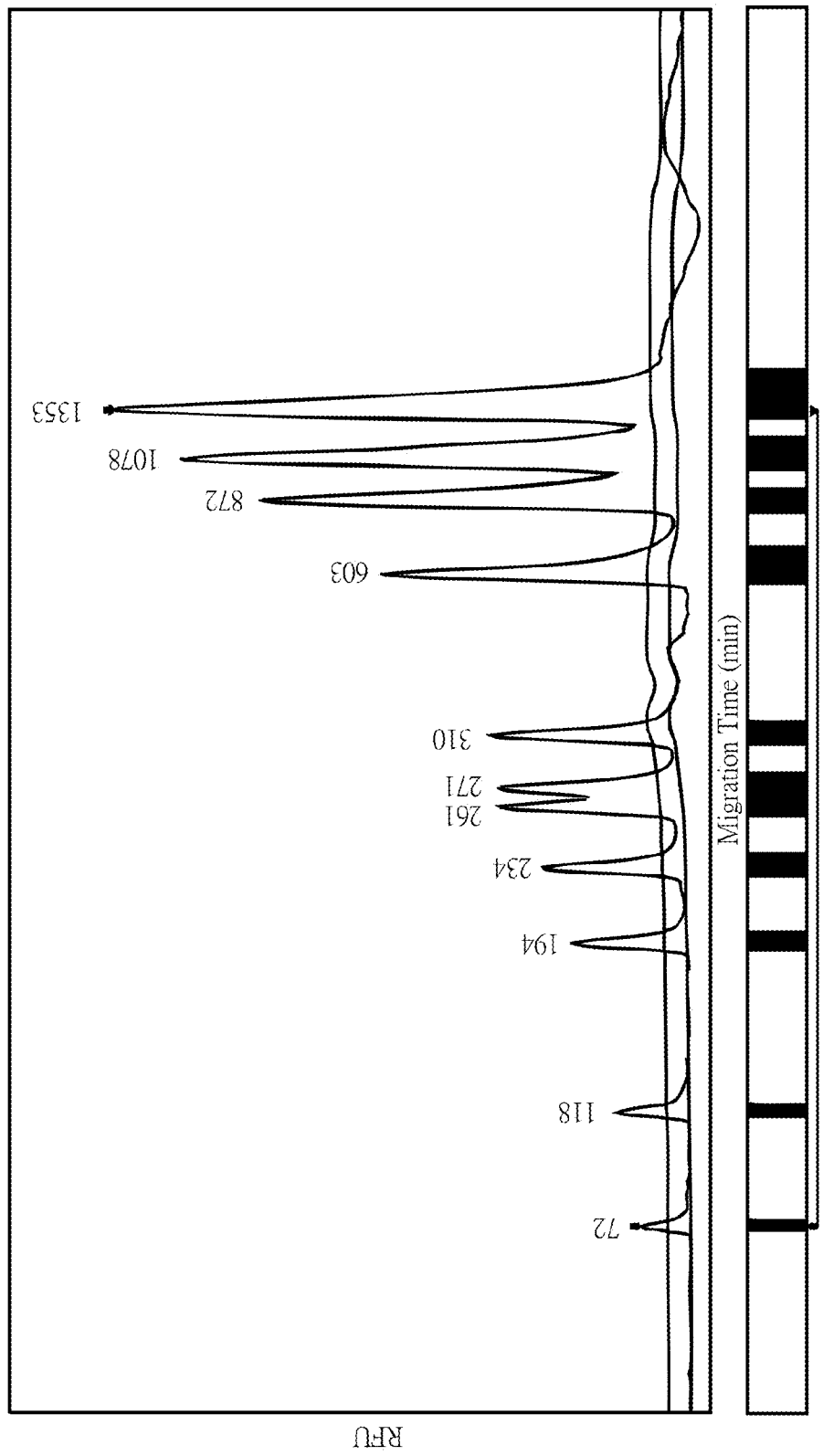
FIG. 13A illustrates the electropherogram representing data of an electrophoresis run.
FIG. 13B represents a corresponding "gel view" of the same data.

The collected data is analyzed by using appropriate application software routines. FIGS. 13A and 13B illustrate the result of one example of fast DNA Fragment separation in less than one minute (60 sec.), to show the high speed separation and high detection sensitivity using a FX174, 50 micron capillary column in the above-described CE instrument. The test conditions are as follows: (a) gel buffer purged for 10-30 seconds; (b) sample injected at 4 KV for 10 sec; and (c) separation at 13 KV, for 60 sec. The gel-chemistry was with Ethidium Bromide dye. The phiX 174 Hae III sample concentration is 5 ng/micro-liter, volume of 10 micro-liter in the sample well. The base pair range is from 72-1553 by with 10 by separation resolution at below 500 by (271-281 bp). The Detection sensitivity is at 0.5 ng/micro-liter with 10:1 S/N for the smallest detectable peak. The graph in FIG. 13A illustrates the detected signal, and the image in FIG. 13B schematically illustrates the separated bands of sample analytes under electrophoresis, simulating a "gel view".

In accordance with the present invention, micro ball-ended fibers provide a very robust design for large volume manufacturing of detectors for CE systems and provides significant background noise reduction, which results in improved S/N with high detection sensitivity in analysis of bio-molecules (e.g., protein, DNA, carbohydrate or immunoassays type analysis).

Given that the excitation and emission fibers 34 and 36 are externally brought within close proximity of the detection zone/window of the capillary column 10 (e.g., by automatic mechanical actuation by manual latching, pneumatic latching, piezo-actuation or solenoid type actuation as discussed below), the capillary cartridge 60 does not need to be provided with any detection optics. External detection optics are coupled to the capillary cartridge 60 when it is installed into a bio-separation instrument. This approach provides simplicity in the capillary cartridge mechanical design, while facilitating automated actuation of ball-ended fibers to engage the capillary cartridge 60. This provides ease in assembly and reduced cost for disposable cartridges.

Other embodiments of integral micro-optical couplings at the end of fibers, such as cone-shaped, round or flat ended types, could also be used for light coupling with the separation channel for reduced background light (noise) and increased sensitivity.

The simplicity of the micro-optical detection also provides flexibility in designing higher throughput (i.e. multi-channel, e.g., 12-channel) type gel-cartridge without the use of optics (excitation or emission optics) inside the cartridge assembly, which makes the new design lower in cost for a true disposable type cartridge product.

Accordingly, the new cartridge based CE system 100 in accordance with the present invention provides simplicity in design, ease of operation and lower cost consumable. It provides a good solution particularly for the research and clinical diagnostic laboratories/industry that demands sustained and stable recurring revenue streams from both an installed base of instruments and recurring need for consumables such as testing reagents and buffer containing capillary cartridge (classical razor/razor blade business model).

The simplicity of this design allows one to incorporate the optical fibers in a mechanical actuator for use with multi-channel, multi-capillary electrophoresis system, which obviates the need to include structures for pre-assembling the fiber or other micro-optics within the multi-channel capillary cartridge design. The flexibility in the optical detection design allows simplicity in cartridge design for 12-capillaries at much reduced cost compared to the capillary cartridge and detection system disclosed in U.S. Pat. No. 6,828,567. With this new design approach by eliminating the optical fibers from inside the capillary cartridge, the overall cost of the assembly could be reduced by a factor that could be 10 to 20 times.

Further, the excitation fiber and emission fiber detection configuration in accordance with the present invention provides additional flexibility in the structure of the overall bio-analysis (e.g., CE) instrument, since the radiation source and the detector modules could be part of the complete instrument assembly or could be used as add on modules outside of the instrument. This kind of flexibility gives the end user the option of interchanging the excitation light source (LED, Laser or other broad band light sources) and/or the emission detector (PMT, Si photodiodes or CCD detectors).

While the invention has been particularly shown and described with reference to the preferred embodiments, it will be understood by those skilled in the art that various changes in form and detail may be made without departing from the spirit, scope, and teaching of the invention.

For example, the excitation radiation source could be, for example, LEDs, Laser Diodes (semiconductor solid-state lasers), pulsed lasers (e.g., solid state lasers, gas lasers, dye lasers, fiber lasers), or other sources of radiation. Alternate relative inexpensive light source for the present invention could be laser diodes in the visible, UV and/or infrared range. For example, laser diodes in the range of 400-900 nm, and more specifically in the range of 400-600 nm may be used, for example.

A person skilled in the art will recognize that the instrument incorporating the essence of this invention can also be used for biomoleculer analysis other than immunoassay and DNA analysis. For example, by altering the separation gel or buffer, the system can also be modified to analyze biomolecules like proteins, carbohydrates, and lipids.

By way of example and not limitation, the detection configuration of the present invention is described in connection with capillary electrophoresis and radiation induced fluorescence detection. It is understood that the present invention is also applicable to detection of analytes separated based on bio-separation phenomenon other than electrophoresis, and detection of radiation emissions other than fluorescence emissions.

Instead of position the excitation fiber and emission fiber substantially coplanar with the axis of the separation channel at the detection zone, the excitation fiber or the emission fiber may be out of plane, without departing from the scope and spirit of the present invention.

Furthermore, while the separation channels in the described embodiments are defined by cylindrical columns or tubes, it is understood that the concepts of the present invention is equally applicable to separation channels defined by open channels, for example micro-channels defined by etching in a substrate.

Accordingly, the disclosed invention is to be considered merely as illustrative and limited in scope only as specified in the appended claims.

The invention claimed is:
1. A cartridge for bio-separation, comprising:
  a body, defining an opening as a detection window for receiving external detection optics;
  at least one capillary column supported in the body, having a first end extending beyond a first end of the body, wherein the detection window exposes a section along the capillary column, to which the external optics are aligned through the detection window; and a reservoir attached to a second end of the body in fluid flow communication with a second end of the capillary column, wherein the reservoir comprises a nipple having a through-hole supporting the second end of the capillary column, wherein the nipple is threaded to a base of the reservoir, wherein the capillary column is supported coaxially by two ferrules that are supported in the body, wherein each of the ferrules is cantilevered by the body and having an end extending into the detection window, and wherein a detection zone along the capillary column is exposed between the extended ends of the ferrules.

2. The cartridge of claim 1, wherein the body is slender and generally longitudinal and cylindrical.

3. The cartridge of claim 2, wherein the capillary column is supported along a central axis of the cylindrical body.

4. The cartridge of claim 3, wherein the body has a body section from which the first end of the body extends, wherein the body section has a width, and wherein the first end of the body is narrower than the width of the body section.

5. The cartridge of claim 4, wherein the first end of the body tapers from the body section to a narrower end.

6. The cartridge of claim 1, wherein the body comprises substantially first and second half shells that are assembled to form the body.

7. The cartridge of claim 1, wherein the body does not include any optical component.

8. The cartridge of claim 1, further comprising a second electrode extending from the first end of the body, wherein the capillary column is coaxially supported within the second electrode, and wherein the second electrode has a first contact surface that is exposed to external through a second electrode opening in the body.

9. The cartridge of claim 1, wherein the reservoir includes a port for introducing pressurized air.

10. The cartridge of claim 1, wherein surface features are provided on the exterior of the body to facilitate positioning and alignment of the cartridge with the external optics.

11. The bio-separation system as in claim 1, wherein the reservoir further comprises a first electrode conductively coupled to content in the reservoir, said first electrode having a contact surface exposed to external of the reservoir through a first electrode opening provided close to the base of the reservoir adjacent to the nipple.

12. A bio-separation system, comprising:
a chassis,
a cartridge as in claim 1, wherein the cartridge body is supported by the chassis, with the first end of the capillary column extending from the cartridge body;
a table support at least a tray containing a sample and a buffer with respect to the extended end of the capillary column;
at least one fork assembly supporting detection optics, wherein the fork assembly is movable to extend into the detection window defined in the cartridge body;
a separation mechanism effecting bio-separation within the capillary column; and
a controller controlling movement of the fork assembly and the separation mechanism to effect separation.

13. The bio-separation system as in claim 12, further comprising a first fork assembly and a second fork assembly, wherein the detection optics comprises first optics supported by the first fork assembly directing incident radiation to a detection zone and second optics supported by the second fork assembly collecting radiation from the detection zone.

14. The bio-separation system as in claim 13, wherein the first and second fork assemblies are positioned on opposite lateral sides of the cartridge, wherein the first and second fork assemblies move between a first position in which the first and second fork assemblies do not extend into the detection window defined in the cartridge, and a second position in which the first and second fork assemblies extend into the detection window defined in the cartridge.

15. The bio-separation system as in claim 12, wherein the chassis supports the cartridge with longitudinal axis of the cartridge body vertical with respect to horizontal plane of the tray.

16. The bio-separation system as in claim 12, further comprising a DC power supply, and wherein the bio-separation system is configured to operate without requiring an AC power source.

17. A cartridge for bio-separation, comprising:
a body, defining an opening as a detection window for receiving external detection optics;
at least one capillary column supported in the body, having a first end extending beyond a first end of the body, wherein the detection window exposes a section along the capillary column, to which the external optics are aligned through the detection window; and
a reservoir attached to a second end of the body in fluid flow communication with a second end of the capillary column,
wherein the capillary column is supported coaxially by two ferrules that are supported in the body, wherein each of the ferrules is cantilevered by the body and having an end extending into the detection window, and wherein a detection zone along the capillary column is exposed between the extended ends of the ferrules, wherein there is no optical element supported in the body which interface the detection zone along the capillary column with the external optics,
wherein the body has a body section from which the first end of the body extends, wherein the body section has a width, and wherein the first end of the body is narrower than the width of the body section,
wherein the first end of the body tapers from the body section to a narrower end,
wherein the body is slender and generally longitudinal and cylindrical, and
wherein the first end of the body is generally conical.

18. The cartridge of claim 17, wherein the body is shaped like a pen.

19. A bio-separation system, comprising:
a chassis,
a cartridge comprising:
a body, defining an opening as a detection window for receiving external detection optics;
at least one capillary column supported in the body, having a first end extending beyond a first end of the body, wherein the detection window exposes a section along the capillary column, to which the external optics are aligned through the detection window; and
a reservoir attached to a second end of the body in fluid flow communication with a second end of the capillary column,
wherein the cartridge body is supported by the chassis, with the first end of the capillary column extending from the cartridge body;
a table support at least a tray containing a sample and a buffer with respect to the extended end of the capillary column;

at least one fork assembly supporting detection optics, wherein the fork assembly is movable to extend into the detection window defined in the cartridge body;

a separation mechanism effecting bio-separation within the capillary column;

a controller controlling movement of the fork assembly and the separation mechanism to effect separation; and a first fork assembly and a second fork assembly, wherein the detection optics comprises first optics supported by the first fork assembly directing incident radiation to a detection zone and second optics supported by the second fork assembly collecting radiation from the detection zone, wherein the first and second fork assemblies are positioned on opposite lateral sides of the cartridge, wherein the first and second fork assemblies move between a first position in which the first and second fork assemblies do not extend into the detection window defined in the cartridge, and a second position in which the first and second fork assemblies extend into the detection window defined in the cartridge, and wherein the capillary column is supported coaxially by two ferrules that are supported in the body, wherein each of the ferrules is cantilevered by the body and having an end extending into the detection window, and wherein the detection zone along the capillary column is exposed between the extended ends of the ferrules, and wherein in the second position, the first and second fork assemblies each has an extended surface that press against the ferrules in the detection window.

20. The bio-separation system as in claim 19, wherein the first and second fork assemblies move along a same axis, and wherein the extended surfaces of the first and second fork assemblies clamp on the ferrules in the second position.

21. The bio-separation system as in claim 20, wherein the extended surfaces of the first and second fork assemblies is groove or concave, facilitating alignment of the extended surfaces against the external surface of the ferrules.

* * * * *